(12) United States Patent
Zhang

(10) Patent No.: US 10,100,702 B2
(45) Date of Patent: Oct. 16, 2018

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 139 days.

(21) Appl. No.: 15/214,171

(22) Filed: Jul. 19, 2016

(65) Prior Publication Data
US 2018/0023448 A1   Jan. 25, 2018

(51) Int. Cl.
| | |
|---|---|
| *G01N 1/00* | (2006.01) |
| *F01N 11/00* | (2006.01) |
| *F01N 3/033* | (2006.01) |
| *G01N 15/06* | (2006.01) |
| *F01N 3/021* | (2006.01) |
| *G01N 1/38* | (2006.01) |
| *F02B 3/06* | (2006.01) |
| *G01N 1/22* | (2006.01) |
| *G01N 1/24* | (2006.01) |
| *G01N 15/00* | (2006.01) |

(52) U.S. Cl.
CPC ............ *F01N 11/00* (2013.01); *F01N 3/021* (2013.01); *F01N 3/033* (2013.01); *G01N 15/0606* (2013.01); *G01N 15/0656* (2013.01); *F01N 2560/05* (2013.01); *F01N 2900/0416* (2013.01); *F02B 3/06* (2013.01); *G01N 1/2205* (2013.01); *G01N 1/24* (2013.01); *G01N 1/38* (2013.01); *G01N 2015/0046* (2013.01)

(58) Field of Classification Search
CPC ................................................ G01N 15/0656
USPC ........................................................ 73/23.33
See application file for complete search history.

(56) References Cited

U.S. PATENT DOCUMENTS

| | | | | |
|---|---|---|---|---|
| 4,630,464 | A * | 12/1986 | Maul ..................... | G01N 1/2258 73/23.33 |
| 2011/0011154 | A1* | 1/2011 | Ante .................... | F02D 41/1466 73/23.33 |
| 2011/0088450 | A1* | 4/2011 | Ante .................... | F02D 41/1466 73/23.33 |
| 2011/0109331 | A1* | 5/2011 | Nelson ................ | F02D 41/1466 324/693 |

(Continued)

OTHER PUBLICATIONS

Zhang, Xiaogang, "Method and System for Exhaust Particulate Matter Sensing," U.S. Appl. No. 14/835,270, filed Aug. 25, 2015, 50 pages.

(Continued)

*Primary Examiner* — Clayton E Laballe
*Assistant Examiner* — Kevin Butler
(74) *Attorney, Agent, or Firm* — Julia Voutyras; McCoy Russell LLP

(57) ABSTRACT

Methods and systems are provided for a particulate matter (PM) sensor assembly positioned downstream of a diesel particulate filter in an exhaust system. In one example, a PM sensor assembly may include a bent tube having a first, upstream end coupled to an exhaust passage, and a second outwardly flared end at a downstream end of the assembly. In this way, the second end of the bent tube may form a venturi that serves to block larger particulates from entering the assembly, and additionally serves to increase exhaust flow into the sensor assembly.

19 Claims, 12 Drawing Sheets

(56) References Cited

U.S. PATENT DOCUMENTS

| | | | |
|---|---|---|---|
| 2011/0232364 A1* | 9/2011 | Koizumi | B01D 46/0057 73/23.33 |
| 2012/0103058 A1* | 5/2012 | Maeda | G01N 15/0656 73/23.33 |
| 2012/0186227 A1* | 7/2012 | Yacoub | G01N 15/0272 60/274 |
| 2012/0297750 A1* | 11/2012 | Sun | F01N 11/00 60/274 |
| 2015/0077350 A1* | 3/2015 | Hinson | G06F 3/044 345/173 |
| 2015/0355066 A1* | 12/2015 | Zhang | G01N 15/0656 73/23.31 |
| 2015/0355067 A1* | 12/2015 | Zhang | G01N 15/0656 73/23.31 |
| 2016/0047731 A1* | 2/2016 | Noda | G01N 15/0656 73/23.33 |
| 2016/0047732 A1* | 2/2016 | Uchiyama | G01N 15/0656 73/23.33 |
| 2016/0153885 A1* | 6/2016 | Kim | G01N 15/0656 73/23.33 |
| 2017/0234786 A1* | 8/2017 | Weber | G01M 15/102 73/23.33 |

OTHER PUBLICATIONS

Zhang, Xiaogang, "Particulate Matter Sensing," U.S. Appl. No. 15/018,637, filed Feb. 8, 2016, 40 pages.

Zhang, Xiaogang, "Method and System for Exhaust Particulate Matter Sensing," U.S. Appl. No. 15/062,384, filed Mar. 7, 2016, 57 pages.

Zhang, Xiaogang, "Method and System for Exhaust Particulate Matter Sensing," U.S. Appl. No. 15/062,449, filed Mar. 7, 2016, 55 pages.

Zhang, Xiaogang, "Method and System for Exhaust Particulate Matter Sensing," U.S. Appl. No. 15/063,703, filed Mar. 8, 2016, 61 pages.

Zhang, Xiaogang, "Method and System for Exhaust Particulate Matter Sensing," U.S. Appl. No. 15/098,751, filed Apr. 14, 2016, 69 pages.

Zhang, Xiaogang, "System for Sensing Particulate Matter," U.S. Appl. No. 15/168,528, filed May 31, 2016, 48 pages.

* cited by examiner

METHOD AND SYSTEM FOR EXHAUST PARTICULATE MATTER SENSING

FIELD

The present description relates generally to methods and systems for sensing particulate matter in an exhaust system.

BACKGROUND/SUMMARY

Engine emission control systems may utilize various exhaust sensors. One example sensor may be a particulate matter (PM) sensor, which indicates particulate matter mass and/or concentration in the exhaust gas. In one example, the PM sensor may operate by accumulating particulate matter over time and providing an indication of the degree of accumulation as a measure of exhaust particulate matter levels. The PM sensor may be located upstream and/or downstream of a diesel particulate filter, and may be used to sense particulate matter loading on the particulate filter and diagnose operation of the particulate filter.

PM sensors may encounter issues with non-uniform deposition of soot on the sensor due to a bias in flow distribution across the surface of the sensor. Further, PM sensors may be prone to contamination from an impingement of water droplets and/or larger particulates present in the exhaust gases. If larger particulates adhere to electrodes of the sensor, the PM sensor may no longer be able to reliably measure the PM quantity passed through the DPF. If the condensed water adheres to the electrodes of the sensor element, for example, the accuracy of the PM sensor may be compromised. In addition, the condensed water adhering to the sensor element may cause the sensor element to get cracked due to thermal stress. This can result in warranty issues.

Various approaches have been developed to reduce the non-uniform deposition of soot on PM sensors. One example PM sensor is shown by Zhang et al. in US 2015/0355067 A1. Therein, the PM sensor includes a cylindrical protection tube having perforations, and a sensor element is positioned inside the tube facing towards the perforations. The PM sensor is fixed to an exhaust passage downstream of a particulate filter in such a way that the perforations are located on a downstream surface of the protection tube, facing towards a tail end of the exhaust passage. In such a configuration, exhaust gas flowing through the exhaust passage may experience pressure variations along the exterior of the protection tube. Because of the higher static pressure at the downstream surface relative to the side surfaces, exhaust gas may be drawn towards the perforations on the downstream surface of the protection tube, and the exhaust may enter the PM sensor via the perforations in a direction opposite to the direction of exhaust flow inside the exhaust passage. Because of their larger momentum, the larger particulates and the water droplets may not be able to undergo a reversal in direction of flow and enter the PM sensor.

However, the inventors herein have recognized potential issues with such systems. As one example, the amount of exhaust gas flowing into the PM sensor may be limited by the size, and shape of the perforations. In addition, since the exhaust gas has to undergo a complete reversal in flow direction to enter the PM sensor, the flow rate of exhaust gas entering the sensor may be reduced. This may, in turn, lead to reduced sensitivity of the PM sensor.

In one example, the issues described above may be addressed by a particulate matter (PM) assembly comprising a bent tube having a first closed end and a second outwardly flared end, a plurality of perforations formed proximate to the first end, and a sensor element positioned facing towards the plurality of perforations, the sensor element located upstream of the second end. In this way, the second end of the bent tube may form a venturi that serves to block larger particulates from entering the assembly, and additionally serves to increase exhaust flow into the sensor assembly. As a result, the sensitivity of the sensor may be increased.

As one example, an exhaust PM sensor assembly may be configured with sensor electrodes and may be positioned downstream of a particulate filter in an exhaust pipe. The PM sensor assembly may include a bent, protection tube that forms an L-shape. A first end of the bent tube may be closed, and coupled to the exhaust pipe. A sensor element may be positioned inside the assembly in front of a plurality of perforations; the sensor element, and the plurality of perforations are both located closer to the first end. A second end of the bent tube may be an open, outwardly flared end and may be located downstream of the first end (and the sensor element) and positioned within the exhaust pipe. The bent tube may have a uniform cross-section over the entire length, except at the second end. At the second end, the tube may include an outwardly angled portion that has increasing cross-section all the way to the tip of the bent tube, thus forming a venturi at the second end of the bent tube. As such, at the venturi, exhaust flows from the tip of the tube where the cross-section is higher, towards the first end of the bent tube with the smaller cross-section. As a result, the exhaust encounters a constriction within which the exhaust flow velocity is increased. The exhaust is then directed from the venturi that is located at the second end through the plurality of perforations towards the sensor element that is located proximate to the first end of the protection tube. Specifically, the exhaust is directed towards electrodes of the sensor element. When a controller applies a voltage across the electrodes of the sensor element, the particulates in the exhaust may be captured across the electrodes. Thus, an increased exhaust flow into the venturi may translate into an increased PM deposition across the electrodes of the sensor element. Thereby, the PM sensor may give an accurate measure of the exhaust particulates in the exhaust passage upstream of the particulate filter. In this way, the PM sensor may be used to diagnose leaks in the particulate filter in a reliable manner. When a soot load on the electrodes reaches a threshold soot load, the controller may apply a voltage to heat a heating element coupled to the sensor element to burn off the particulates deposited on the electrodes, thus regenerating the PM sensor.

In this way, by creating a venturi-like structure inside the PM sensor assembly, the exhaust flow inside the PM assembly may be increased, with a corresponding increase in sensor sensitivity. In addition, as the exhaust is streamed from the downstream side of the bent tube, the amount of larger particulates and/or water droplets impinging on the sensor element may be reduced. Specifically, due to their larger momentum, water droplets and/or larger particulates may flow past the venturi without redirecting their flow direction to enter the venturi. Therefore, the sensor element may be protected from impingement of water droplets and larger particulates. Overall, the functioning of the PM sensor assembly may be improved and PM sensor output may be more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
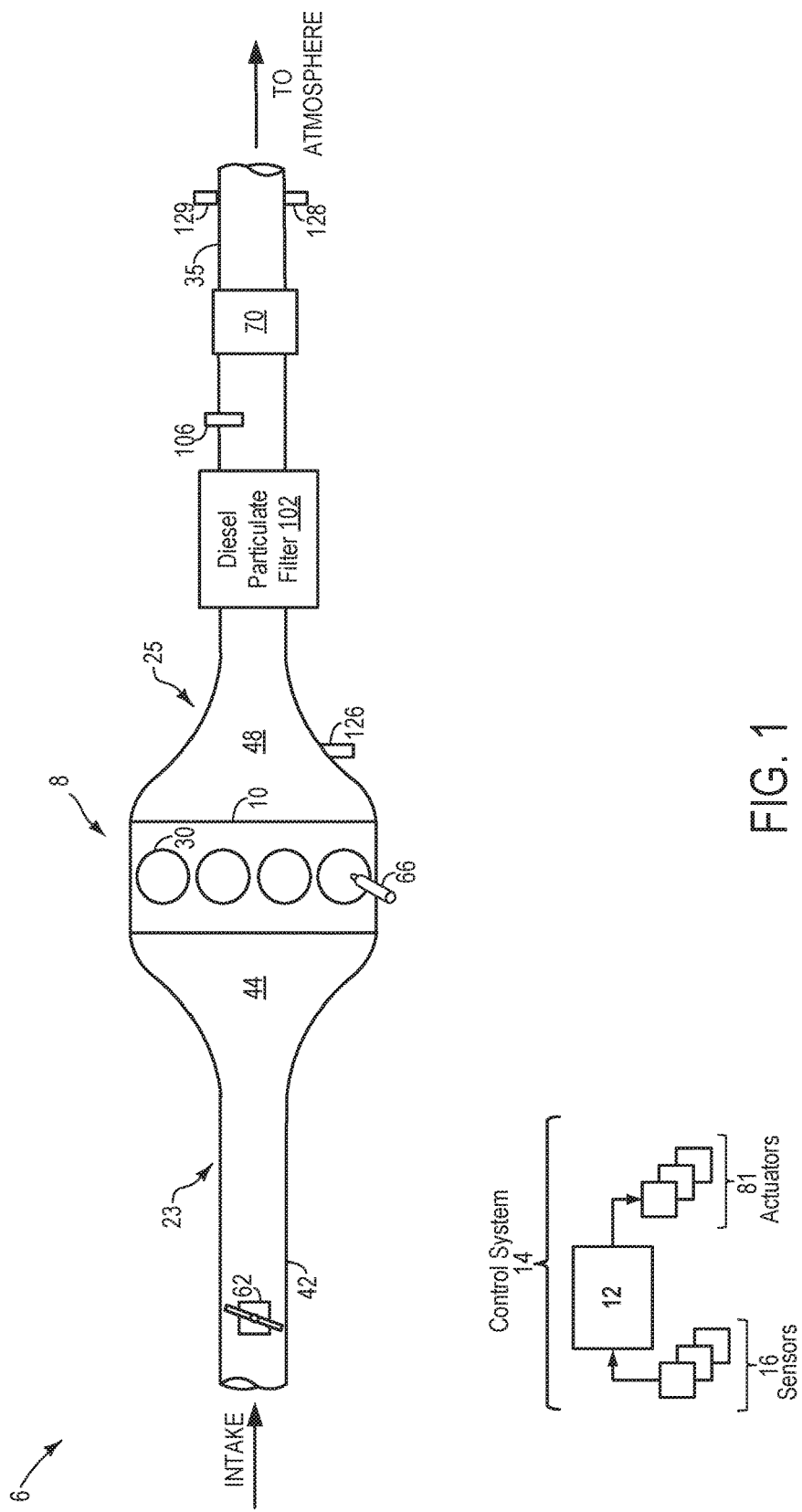
FIG. 1 shows a schematic diagram of an engine and a particulate matter (PM) sensor assembly positioned in an exhaust flow.
Figure 3A:
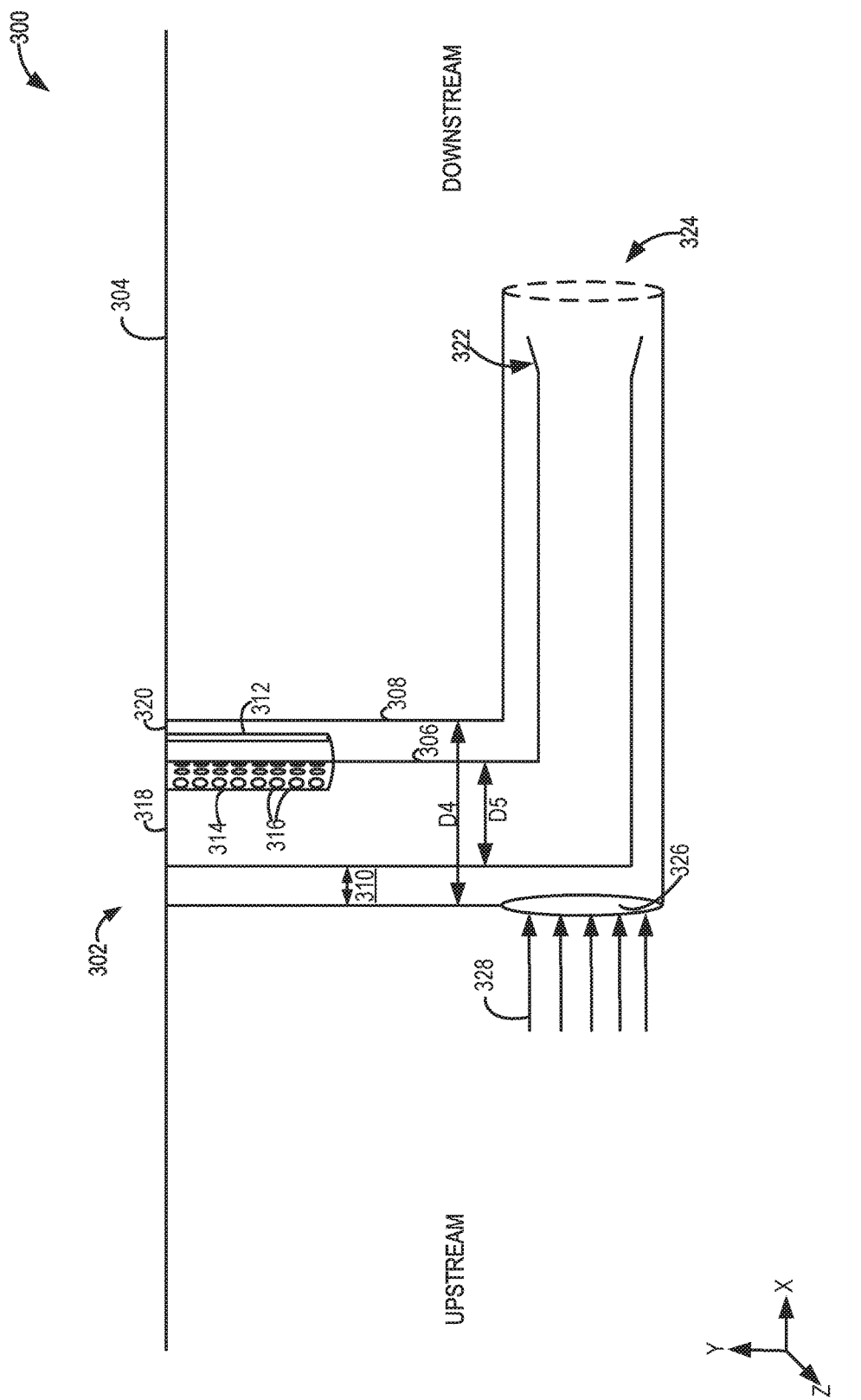
FIG. 3A shows a schematic view of a second example PM sensor assembly having the protection tube as an inner tube placed within an outer, L-shaped tube, and additionally including a plurality of perforations formed on a surface of the inner tube, and a curved sensor element placed in a gap formed between the inner and the outer tubes.
Figure 3B:
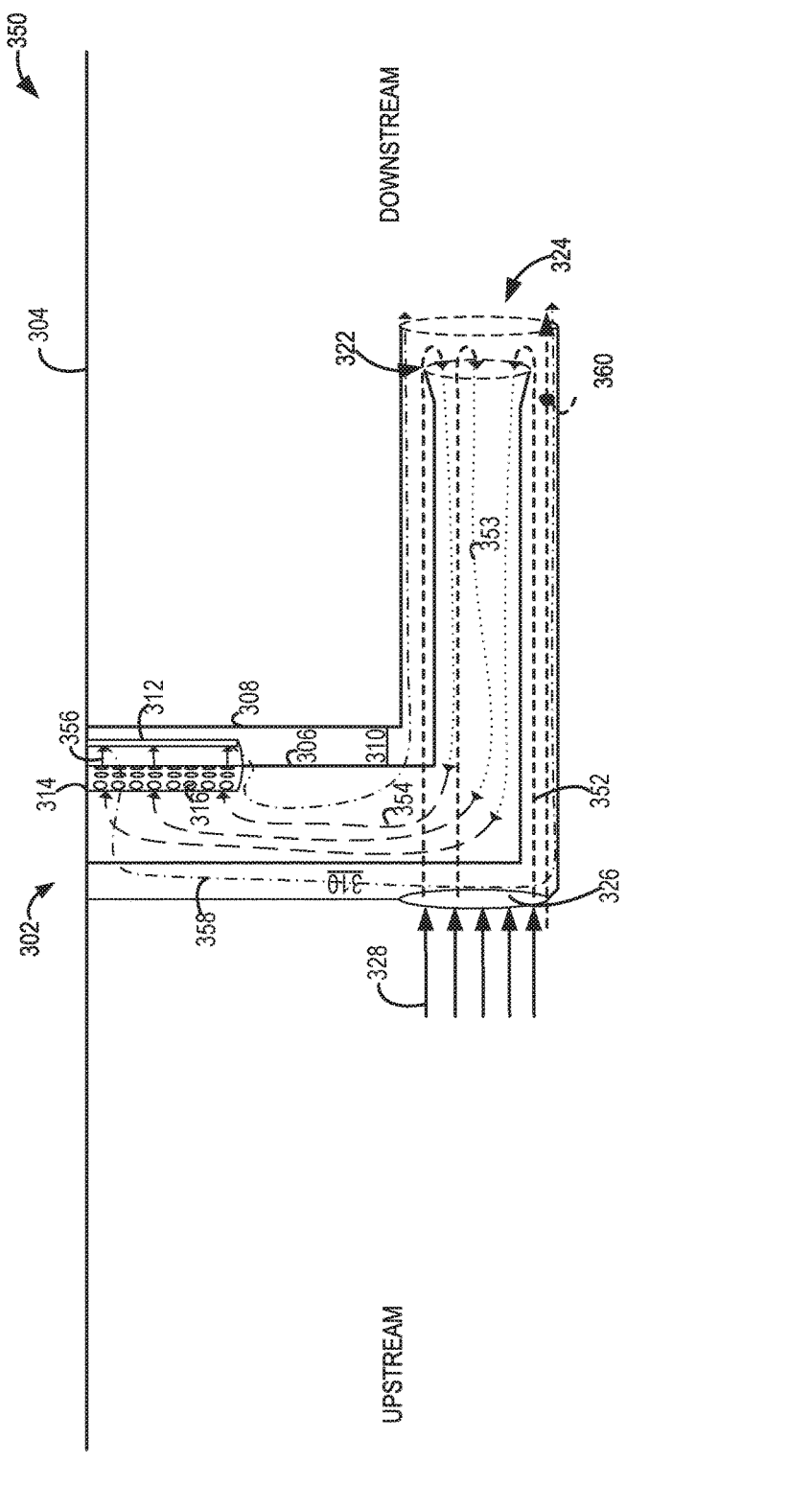
FIG. 3B shows a schematic diagram of the PM sensor assembly showing exhaust flowing into an outlet formed on the outer tube, and reversing the direction of flow to flow into the inner protection tube through the venturi-like opening formed on the inner protection tube.
Figure 4A:
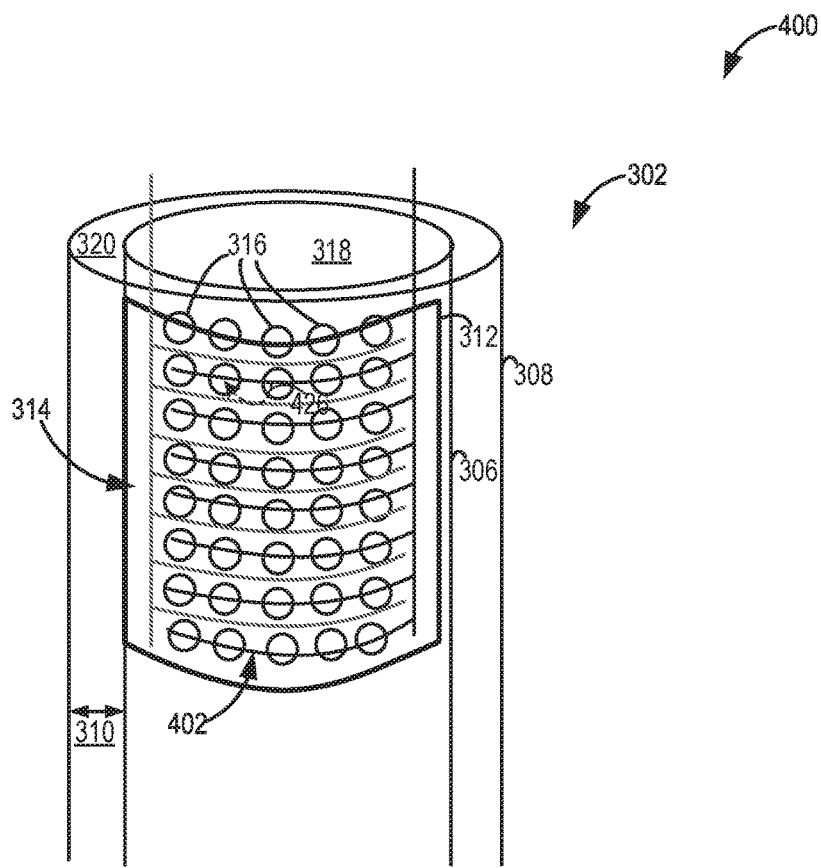
FIG. 4A shows a schematic diagram of plurality of perforations formed on the surface of the inner tube.
Figure 4B:
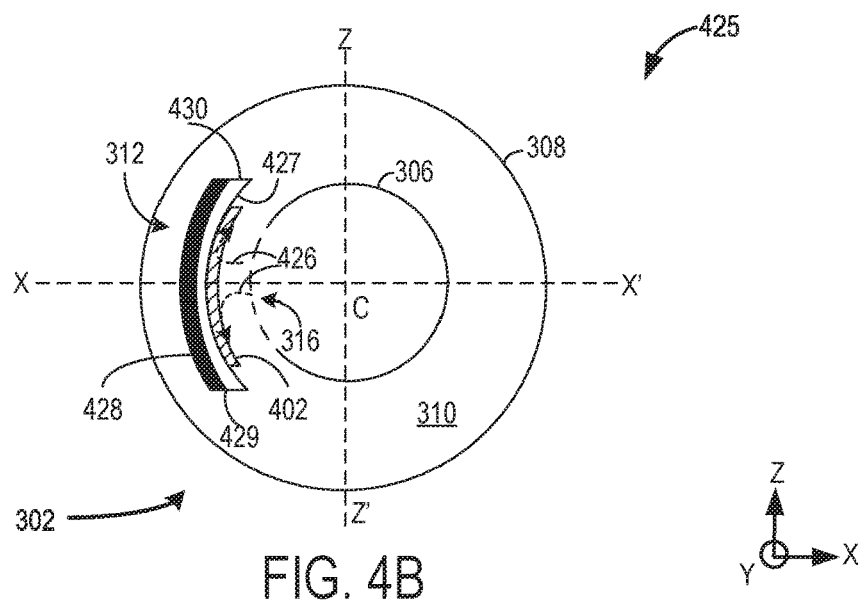
FIG. 4B shows a cross-section of the inner and the outer tubes, and the sensor element positioned within the gap facing towards the plurality of perforations.
Figure 4C:
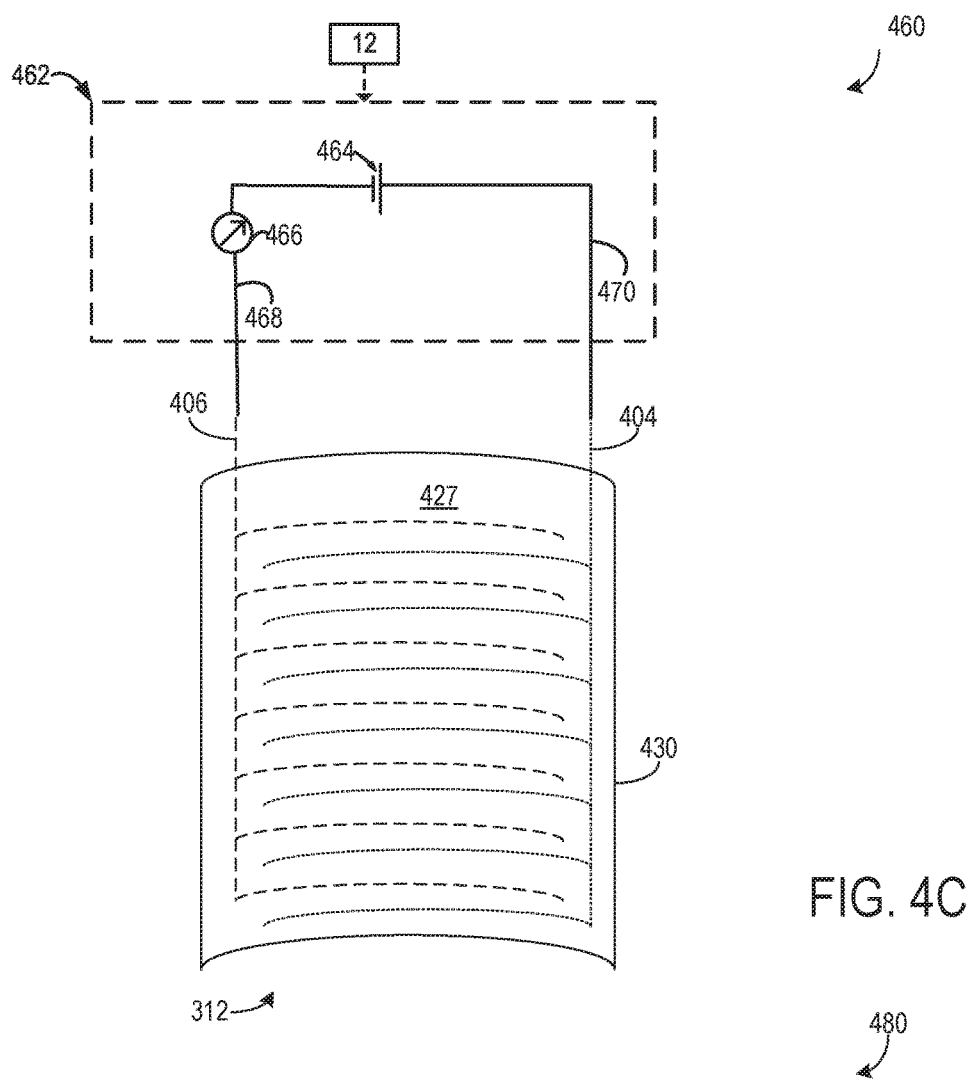
FIGS. 4C-4D show schematic views of the curved sensor element with interdigitated electrodes formed on one side, and a heating element formed on an opposite side of the sensor element.
Figure 4D:
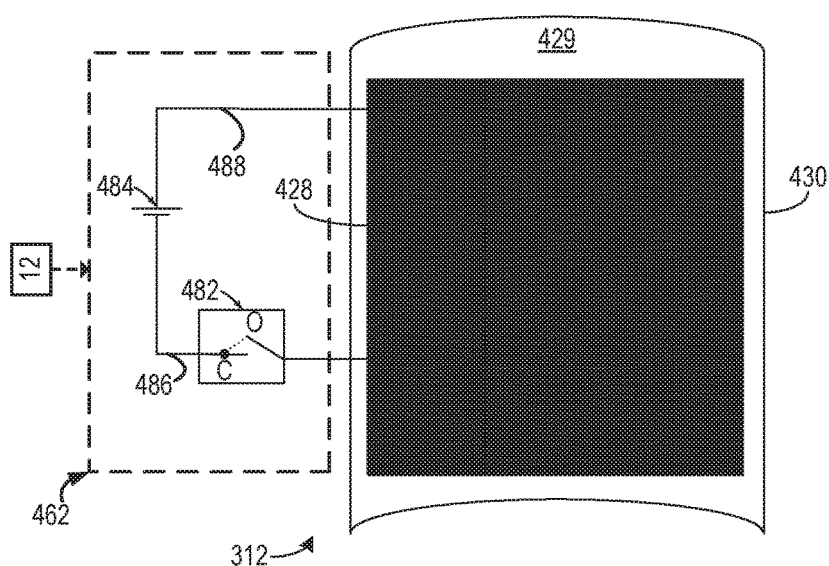

The following description relates to systems and methods for sensing particulate matter (PM) in an exhaust flow of an engine system, such as the engine system shown in FIG. 1. A first example PM sensor assembly shown in FIG. 2A may be coupled to an exhaust passage of the engine system. As such, the PM sensor assembly may include an L-shaped bent protection tube coupled to the exhaust passage via a first, closed end. In addition, the bent tube may include a second outwardly flared up (FIG. 2C) end placed within the exhaust passage. Herein, the second end may serve as an opening configured to direct exhaust from the exhaust passage into the PM sensor assembly (FIG. 2B). Specifically, the exhaust flows towards a sensor element through a plurality of perforations formed on a baffle. As such, the second end may include a venturi-like opening configured to increase exhaust flow at the opening of the PM sensor assembly. A second example PM sensor assembly may include the bent tube shown in FIG. 2A as an inner tube. The inner tube may be positioned within an outer L-shaped bent tube and separated from the outer tube by a gap as shown in FIG. 3A. An opening formed proximate on the outer tube may be configured to first direct exhaust into the gap between the inner and the outer tube, and then into the second end of the inner tube. As before, the second end may include a venturi-like opening configured to increase exhaust flow into the inner tube from the gap. Once inside the inner tube, the exhaust may flow towards a plurality of perforation formed on a surface of the inner tube towards a sensor element positioned within the gap as shown in FIG. 3B. The sensor element may be curved sensor with interdigitated electrodes formed on a surface facing towards the plurality of perforations as shown in FIGS. 4A and 4B. As such, the sensor element may be a curved element with interdigitated electrodes formed on a first side (FIG. 4C), and a heating element formed on a second, opposite surface (FIG. 4D). The examples PM sensor assemblies may include a controller configured to perform a control routine, such as an example routine of FIG. 5 to accumulate exhaust particulates in the exhaust flow across electrodes of the sensor element. The controller may intermittently clean the PM sensor assembly (FIG. 6) to enable continued PM monitoring. Furthermore, the controller may be configured to perform a routine, such as an example routine of FIG. 7 to regenerate the exhaust particulate filter based on a time between PM sensor regenerations. An example of filter diagnostics is shown in FIG. 8. In this way, the functioning of the PM sensor to estimate the filtering capabilities of the DPF (and thereby to detect DPF leaks) may be increased.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor assembly rotation, switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. As an example, while operating the PM sensor to accumulate soot particulates, the controller send a control signal to an electric circuit to apply a voltage to electrodes of a sensor element of the PM sensor assembly to trap the charged particulates onto the surface of sensor electrodes of a sensor element. As another example, during PM sensor assembly regeneration, the controller may send a control signal to a regeneration circuit to close a switch in the regeneration circuit for a threshold time to apply a voltage to a heating element coupled to electrodes to heat the electrodes of the sensor element. In this way, the electrodes are heated to burn off soot particles deposited on the surface of the electrodes. Example routines are described herein with reference to FIGS. 5-7.

Figure 2A:
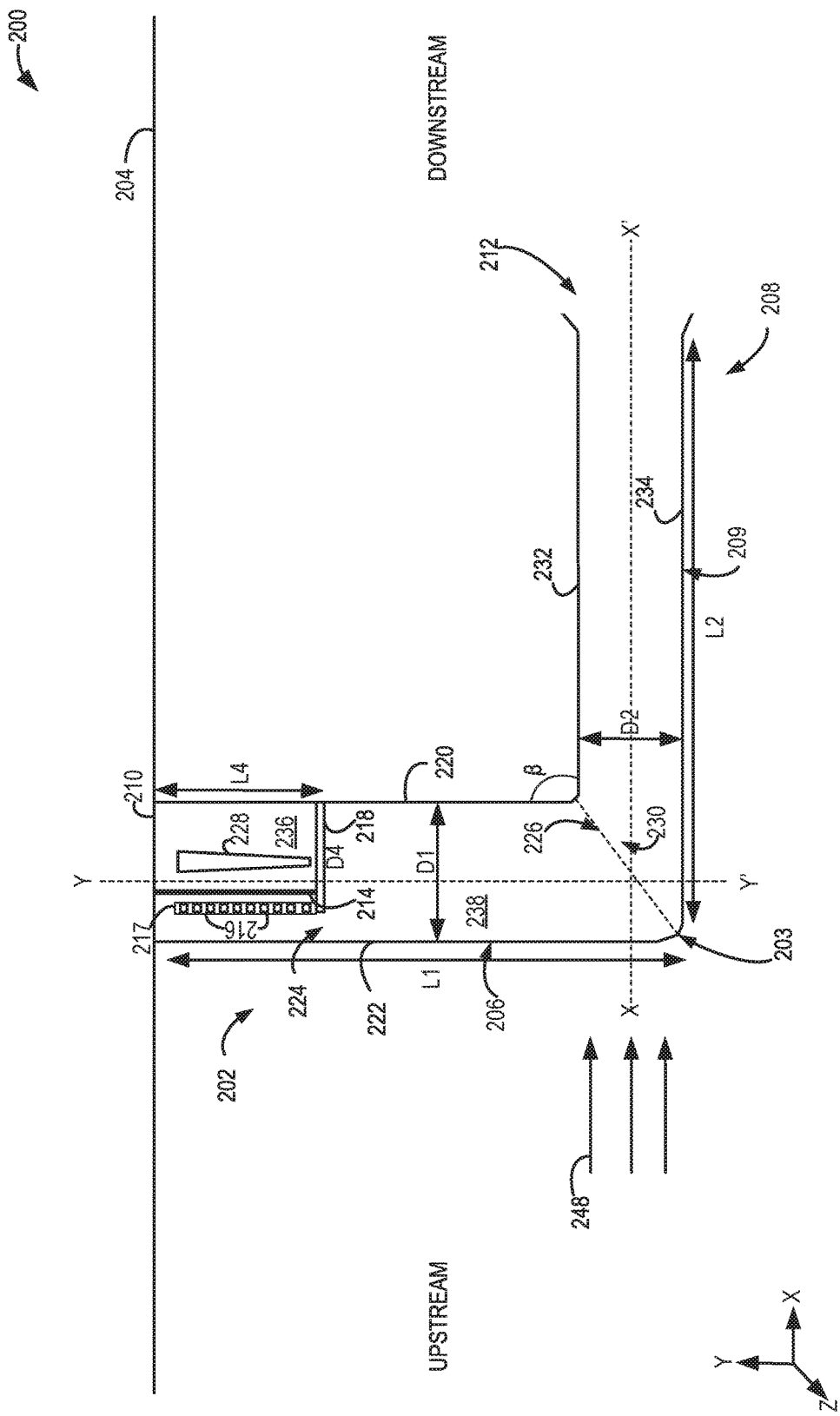
FIG. 2A shows a schematic view of a first example PM sensor assembly having an L-shaped protection tube with a venturi-like inlet, and a baffle having a plurality of perforations positioned proximate to a sensor element, wherein both the baffle and the sensor element are positioned within the protection tube.
Figure 2B:
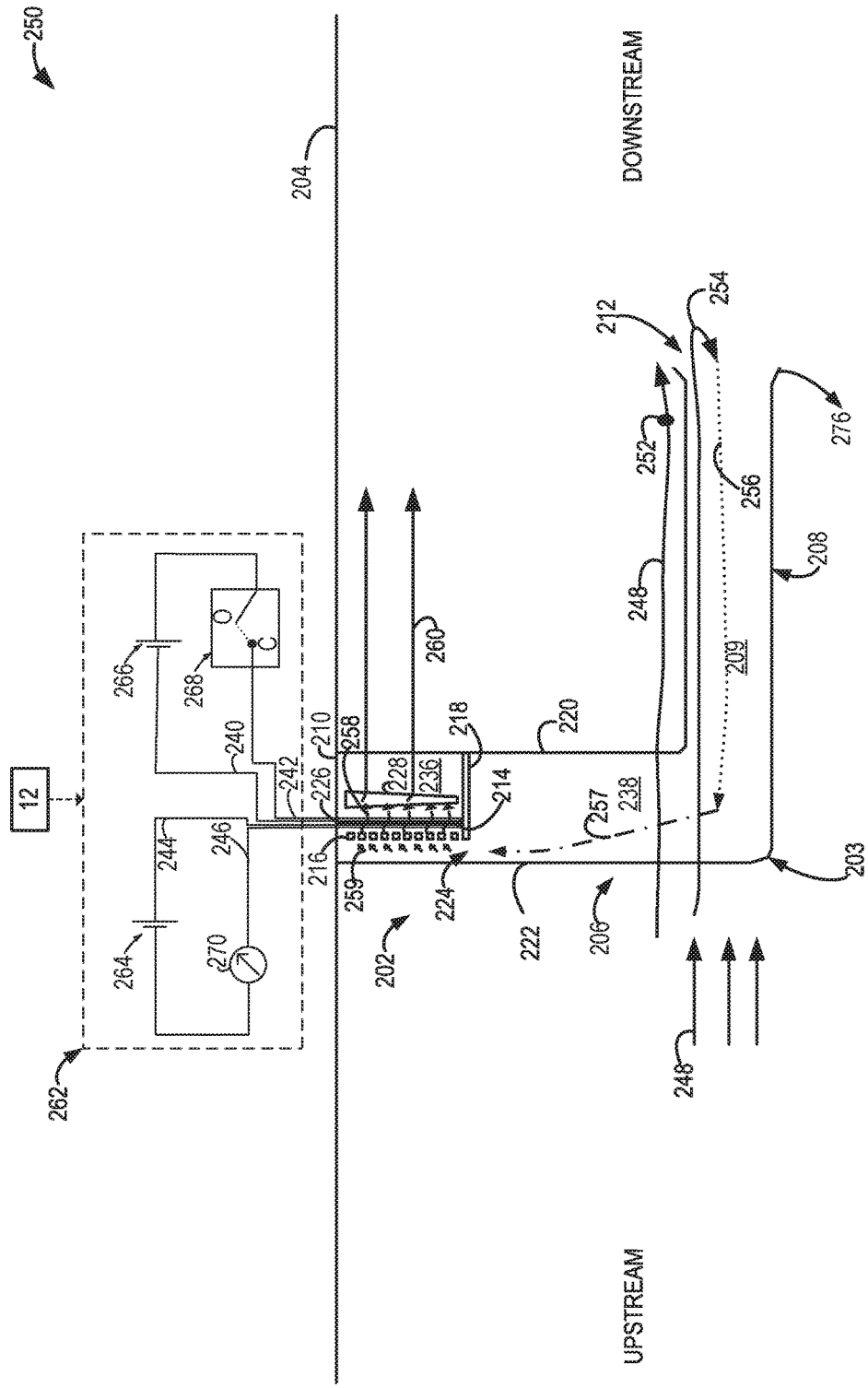
FIG. 2B shows a schematic diagram of the PM sensor assembly showing flowing into the L-shaped protection tube through the venturi-like opening formed on the protection tube.

Turning now to FIG. 2A, a schematic view 200 of an example embodiment of a particulate matter (PM) sensor assembly 202 (such as PM sensor 106 of FIG. 1) is shown. The PM sensor assembly 202 may be configured to measure PM mass and/or concentration in the exhaust gas, and as such, may be coupled to an exhaust passage or pipe 204 (e.g., such as the exhaust passage 35 shown in FIG. 1), upstream or downstream of a diesel particulate filter (such as DPF 102 shown in FIG. 1).

In the schematic view 200, the PM sensor assembly 202 is disposed inside the exhaust passage 204 with exhaust gases flowing (along X-axis) from downstream of the diesel particulate filter towards an exhaust tailpipe, as indicated by arrows 248. With reference to the PM sensor assembly 202, exhaust flows from an upstream side towards a downstream side of the assembly in the direction indicated by arrows 248. For example, the downstream side may be closer to an exhaust tailpipe. An axis system is shown comprising three axes, namely, an x-axis parallel to the horizontal direction, a y-axis parallel to the vertical direction, and a z-axis perpendicular to the x- and y-axes. The axis system shown on the view 200 may be used to describe the relative positioning of components of the PM sensor assembly 202. A "height/length" of the PM sensor assembly 202 and/or its components may be used to define the extent of the components along the y-axis. Similarly, a "length/diameter" of components of the PM sensor assembly 202 may be used to refer to the physical extent of the components along the x-axis. The physical extent of components along the z-axis may be referred to as a "width."

The PM sensor assembly 202 includes a bent tube (or bent tube assembly) 203 that forms an L-shaped protection tube or housing. The PM sensor assembly 202 includes a sensor element 214 positioned inside the bent tube 203. As such, the sensor element 214 is positioned inside the walls (not protruding) of the bent tube 203. By placing the sensor element 214 entirely inside the bent tube 203, the electrodes of the sensor element 214 may be shielded from the harsh environment within the exhaust passage 204, enhancing the overall functioning of the sensor element 214.

The bent tube 203 includes a first tube (or portion) 206 fluidically coupled to a second tube (or portion) 208. As such, the first tube 206 is a hollow cylindrical tube of length L1 and diameter D1 with a central axis Y-Y' orthogonal to exhaust flow inside the exhaust passage (indicated by arrow 248). Hereafter, the first tube 206 may also be referred to as a vertical tube/portion. The first tube 206 may include a straight portion of length L1 of uniform cross-section. Specifically, the diameter D1 of the first tube 206 may be the same throughout the length L1 of the first tube 206.

The first tube 206 includes a first, closed end 210 that is coupled to the exhaust passage 204, and a second open end 226 that is fluidically coupled to the second tube 208. Exhaust flowing inside the exhaust passage 204 may not be able to enter the PM sensor assembly 202 via the first end 210 due to the first end being closed. However, since the second end 226 is not closed, but is coupled to the second tube 208, exhaust may flow though the second end 226 of the first tube 206. The first tube 206 may include a first vertical surface 222 (e.g., upstream facing wall/surface) extending to a length L1 from the top of the exhaust passage 204 downwards (parallel to Y-axis) inside the exhaust passage 204. The first tube 206 may additionally include a second, vertical surface 220 (e.g., downstream facing wall/surface) extending to a length L1' from the top of the exhaust passage 206, parallel to the first vertical surface 222, into the exhaust passage 204. As such, L1' may be smaller than L1 (see below). Herein, the central axis Y-Y' of the first tube may vertical, and as such may be oriented in the direction of gravitational force; the gravitational force defined as the force acting on the PM sensor assembly positioned inside an exhaust passage of a vehicle, when the vehicle is on the ground (flat, not at an incline) and the vehicle is not moving.

The second tube 208 of the PM sensor assembly 202 includes a hollow cylindrical tube of length L2 and diameter D2 (straight portion 209) with a portion of varying diameter (non-uniform portion) at a second end 212. The second tube 208 has a central axis X-X' orthogonal to the central axis Y-Y' of the first tube 206. Further, the central axis X-X' of the second tube is parallel to the direction of exhaust flow inside the exhaust passage (indicated by arrow 248). Herein, the straight portion 209 of diameter D2 and length L2 is a hollow cylindrical tube of uniform cross-section, having the same diameter D2 throughout the length L2. The second end 212 may be interchangeably referred to as the non-uniform portion of the second tube 208, with increasing cross-section, as described with reference to FIG. 2C.

Hereafter, the second tube 208 may also be referred to as a horizontal tube/portion. To elaborate, the second tube 208 may extend in a direction parallel to exhaust flow inside the exhaust passage, orthogonal to the first tube 206. The second tube 208 includes a first end 230 that is fluidically coupled to the second end 226 of the first tube 206. Specifically, the vertical surface 220 (e.g., downstream facing wall/surface) of the first tube 206 is coupled to a horizontal surface 232 (e.g., top wall/surface) of the second tube 208. Likewise, the vertical surface 222 (e.g., upstream facing wall/surface), of the first tube 206 is coupled to a horizontal surface 234 (e.g., bottom wall/surface) of the second tube 208. The vertical surface 222 may be closer to the particulate filter (PF) than any other surface of the PM sensor assembly 202 when positioned in an exhaust passage, such as exhaust passage 35 shown in FIG. 1, where the PF is positioned upstream of the PM sensor assembly 202. Herein, the length of the vertical surface 222 may be equal to L1, while the length of the vertical surface 220 may be equal to L1–D2, where D2 is the diameter of the uniform portion of the second tube 208. Similarly, the length of the horizontal surface 234 may be equal to L2, while the length of the horizontal surface 232 may be equal to L2–D1, where D1 is the diameter of the first tube 206.

In one example, the length and diameter of the first and the second tubes may be equal. In another example, the first and the second tubes may be of unequal lengths and/or diameters. The bent tube 203 may be manufactured from a single hollow cylindrical tube that is bent along the length (e.g., midway, or one-thirds, or two-thirds) of the tube at an angle that is close to 90° (e.g., from 85 to 95 degrees), thus forming the L-shape of the bent tube 203. The first tube and the second tube form a contiguous L-shaped tube.

In yet another example, the first tube and the second tube may be coupled together to form a single contiguous L-shaped tube wherein the first tube 206 includes a circular cutout of diameter D2 formed on the vertical surface 220 of the first tube proximate to the second end 226, and the second tube 208 includes a circular cutout of diameter D1 formed on the horizontal surface 232 closer to the first end 230 of the second tube 208. The vertical surface 222 of the first tube 206 may be coupled (e.g., welded) to the horizontal surface 234 of the second tube 208 closer to the first end 230 of the second tube 208. The vertical surface 220 of the first tube may be coupled (e.g., welded) to the horizontal surface 232 of the second tube 232 closer to the first end 230 of the second tube 208. In this way, the bent tube 203 may be formed, and the first tube 206 may be in fluidic communication with the second tube 208.

In one example, the first tube 206 and the second tube 208 may be at angle 90° relative to each other. In such an example, the angle β enclosed between the central axes of the first tube 206 and the second tube 208 is 90°. Herein, the angle β additionally refers to the angle enclosed between the vertical surface 220 of the first tube 206, and the horizontal surface 234 of the second tube 208, and that enclosed between the vertical surface 222 of the first tube 206, and the horizontal surface 232 of the second tube 208. In other examples, the first tube 206 and the second tube 208 may not be perpendicular to one another, however the tubes may be at an angle with respect to each other. Thus, the angle β may be within a range given by 0<β<180°.

The second tube 208 includes the second outwardly flared end 212 that is downstream of the first end 210. Herein, the second end 212 of the second tube 208 is an open end that is positioned downstream of the second end 226 of the first tube 206, and first end 230 of the second tube 208. In addition, the second end 212 of the second tube 208 is not coupled to any of the first end 210 of the first tube 206, the second end 226 of the first tube 206, and the first end 230 of the second tube 208. The second end 212 of the second tube 208 is an open end that serves as an inlet of the PM sensor assembly 202, which will be described in detail with reference to FIG. 2C. Thus, exhaust may enter the PM sensor assembly 202 only via the opening formed at the second end 212 of the second tube 208.

Figure 2C:
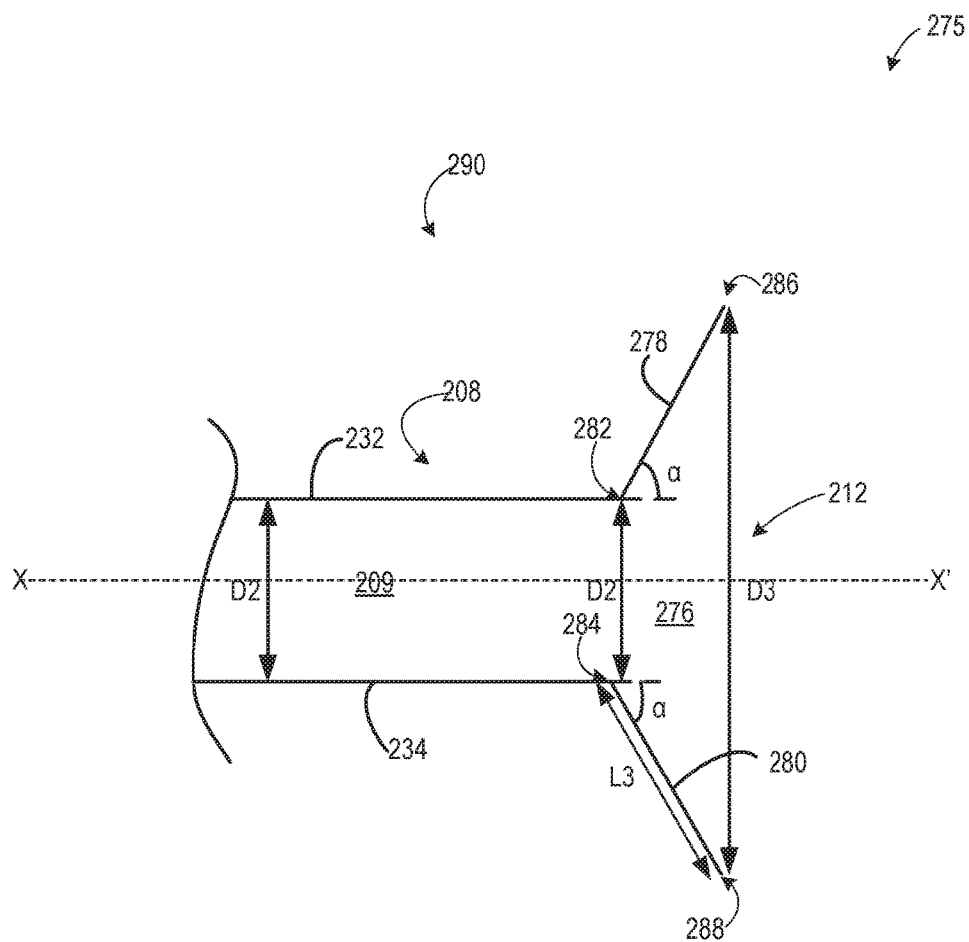
FIG. 2C shows an exploded view of the venturi-like opening formed at an end of the protection tube.

Turning now to FIG. 2C, an exploded view 275 of the second end 212 of the second tube 208 is shown. As such, components previously introduced in FIG. 2A are numbered similarly in FIG. 2C. The second end 212 includes outwardly flared flanges 278 and 280 coupled to horizontal surface 232 and 234 of the second tube 208 respectively. Herein, the horizontal surface 232 and 234 are the respective top and bottom surfaces/walls of the straight portion 209 of the second tube 208. A distance D2 separates the two horizontal surfaces 232 and 235 from each other. Specifically, the flange 278 may be coupled to the horizontal surface 232 at end 282 of the straight portion 209 of the second tube 208 at an angle +α with respect to the central axis X-X'. Likewise, the flange 280 may be coupled to the horizontal surface 234 at end 284 of the straight portion 209 of the second tube 208 at an angle −α with respect to the central axis X-X'. Herein, the positive sign for the angle α represents an angle measured in the anti-clockwise direction, and the negative sign for the angle α represents an angle measured in the clockwise direction. Thus, the flange 278 is rotated away from the flange 280 (and the central axis X-X') in the anti-clockwise direction, and the flange 280 is rotated away from the flange 274 (and the central axis X-X'), however in an opposite (e.g., clockwise) direction. In one example, the second end 212 may be described as a hollow cone 276 with a diameter D2 at an innermost end (end that is coupled to the straight portion 209, for example), and a diameter D3 at the outermost end. Herein, D3>D2, thus, the outer cross-section of the cone 276 is greater than the inner cross-section of the cone 276. Thus, the second end includes a portion of increasing area and thus, increasing cross-section. The slope of the flanges (or angle α) may depend on the diameters D2 and D3 of the hollow cone, and the length L3 of the flanges 278 and 280 (also referred to as sides of the cone 276). Mathematically, the angle α can be written as equation (1) shown below:

$$\sin\alpha = \frac{(D3-D2)}{2*L3} \quad (1)$$

In one example, the value of a may be fixed, at 30°, for example. In other examples, the value of α may be adjustable. In such an example, the flanges may be plates coupled to the straight portion of the second tube via a hinge and a motor. A controller (such as controller 12 of FIG. 1) may be able to rotate each of the flanges about the central axis X-X' to adjust the angle α, by adjusting an output level of the motor coupled to the plates. In this way, the cross-section of the opening to the PM sensor assembly 202 may be adjusted based on exhaust flow conditions. In one example, when exhaust flow rate inside the exhaust passage decreases below a threshold, the controller may actuate the motors to rotate the flanges outward to increase a, to increase the cross-section of the opening to the PM sensor assembly 202. This in turn, increases the rate of exhaust flow into the PM sensor assembly via the opening. Thus, the exhaust PM may be accumulated at an increased rate across the sensor element, when exhaust flow rate is decreased inside the exhaust passage.

Together, the straight portion 209, and the second end 212 forms a venturi 290. Herein, the venturi is formed at the end of the second tube 208 by joining the hollow cone 276 to the straight portion 209 of the second tube 208. The venturi 290 serves as an inlet to the PM sensor assembly 202. The advantage of using the venturi 290 as the inlet is that exhaust flowing into the PM sensor assembly has to flow through a pipe of decreasing diameter, which in turn causes the velocity of the exhaust flow inside the venturi to increase. Thus, the amount of exhaust flowing into the PM sensor assembly 202, specifically towards the sensor element 214 positioned there within is increased.

Returning to FIG. 2A, the sensor element 214 of the PM sensor assembly 202 is positioned inside the first tube 206 as shown in schematic view 200. In one example, a bottom end of the sensor element 214 may be coupled to the bottom seal 218, and a top end of the sensor element 214 may be coupled to the first end 210 of the inner tube 206. Specifically, the first tube 206 may include a bottom seal or plate 218 at a distance L4 from the first end 210 of the first tube, and the sensor element 214 may be positioned within the space enclosed between the first end 210 of the first tube 206, and the bottom seal 218. The bottom seal 218 may be a plate of length D4 having a longer axis that is orthogonal to the central axis of the first tube 206. One end of the bottom seal 218 may be coupled to vertical surface 220 of the first tube, and the other, opposite end of the bottom seal may be separated from the opposite vertical surface 222 of the first tube 206 by a gap 224. The bottom seal 218 divides the first tube 206 into two chambers, an upper chamber 236, and a lower chamber 238. The upper chamber 236 refers to the region of the first tube 206 enclosed between the first end 210 of the first tube 206, and the bottom seal 218. The gap 224 that separates the bottom seal 218 from the vertical surface 222 of the first tube 206 allows fluidic coupling of the upper chamber 236 with the lower chamber 238. In one example, the lower chamber 238 may refer to the region within the first tube 206 that is below the bottom seal 218, and additionally includes the entire region enclosed within the second tube 208. The sensor element 214 may be positioned inside the upper chamber 236 such that a longer axis of the sensor element 214 is parallel to the central axis Y-Y' of the first tube 206. Thus, the sensor element 214 is orthogonal to the bottom seal 218.

The PM sensor assembly 202 may additionally comprise a plurality of perforations 216 formed on a baffle 217. The plurality of perforations 216 may be positioned closer to the sensor element 214, and further away from the second end 212 of the second tube 208. Specifically, the plurality of perforations 216 may be upstream of the sensor element 214 proximate to the gap 224.

The sensor element 214 is separated from the baffle 217, and thus the plurality of perforations 216 by a distance (1 mm to 3 mm, for example). Thus, the sensor element is not in contact with the baffle and the plurality of perforations. The distance of separation between the sensor element and the baffle may be smaller than the gap 224, for example. The arrangement of the baffle with plurality of perforations, and location and orientation of the sensor element with respect to the baffle, allows for increased vertical distribution of soot deposition on the electrodes of the sensor element. Herein, the arrangement causes the exhaust flow distribution to be uniform along the vertical direction (Y-axis).

The plurality of perforations includes a series of holes or orifices formed on the baffle 217 that allow exhaust to flow towards the sensor element 214 as described with reference to FIG. 2B. Various geometries and spacing of the holes may be possible. Some example geometries of the holes include, but are not limited to, cylindrical, spherical, square, rectangular and the like. In one example, there are 10 square perforations 216 in a single column. In alternate examples, the perforations 216 may be spaced and arranged differently while still directing flow towards the sensor element 214.

The PM sensor assembly 202 additionally includes outlet 228 formed on a front surface of the first tube 206. In one example, the outlet 228 includes a trapezoid shaped opening configured to allow exhaust to exit the PM sensor assembly 202. Other geometries of the outlet 228 may be used without deviating from the scope of the disclosure. Exhaust flowing into the PM sensor assembly 202 via the second end 212, flows towards the sensor element 214 through the plurality of perforations 216, and thereon flows out of the PM sensor assembly through the outlet 228 as described in FIG. 2B.

Turning now to FIG. 2B, schematic view 250 shows exhaust flow through the PM sensor assembly 202. As such, components previously introduced in FIGS. 2A and 2C are numbered similarly in FIG. 2B. The view 250 depicts exhaust flowing into the PM sensor assembly 202 via the second outwardly flared end 212 of the second tube 208 and thereon through the gap 224 and the plurality of perforations 216 towards the sensor element 214.

The PM sensor assembly 202 is fixed to the exhaust passage 204 downstream of a particulate filter in such a way that the second end 212 is located on a downstream side of the bent tube 203. As such, exhaust gas flowing through the exhaust passage may experience pressure variations along the exterior of the bent tube 203. For example, a higher static pressure may be created at the downstream side of the bent tube 203 than along the vertical side surfaces 220 and 220, and front, and back surfaces of the bent tube 203. Because of the higher static pressure at the downstream side relative to the side surfaces, exhaust gas may be drawn in towards the downstream side of the PM sensor. In particular, the exhaust gases may be drawn towards the second end 212 of the second tube 208 of the PM sensor assembly 202. Since the static pressure on the front and the back surface of the first tube 206 is lower than the static pressure at the downstream side, exhaust may not enter the assembly via the outlet 228, for example. Thus, the exhaust may only enter the PM sensor assembly via the opening of the second end 212 in a direction opposite (arrow 254) to the direction of exhaust flow inside the exhaust passage (arrow 248). Specifically, the structure of the bent tube 203 and the position of the second open end 212 on the downstream side allow the exhaust to reverse the direction of flow and enter into the PM sensor assembly 202.

As described with reference to FIG. 2C, by coupling the straight portion 209 with an end with increasing diameter, the venturi 290 is formed at the second end 212 of the second tube 208. The advantage of forming the venturi 290 at the opening of the PM sensor assembly 202 is that the exhaust that is drawn into the second end 212 undergoes a Venturi effect wherein the velocity of the exhaust increases as it passes through the venturi 290. For example, the exhaust entering the second tube 208 through the venturi 290 flows at a higher rate inside the second tube 208 than the rate at which exhaust is flowing outside in the exhaust passage 204. Said another way, an exhaust flow rate through venturi 290 in second tube 208 is higher than exhaust flow rate through exhaust passage 204. Additionally, since the exhaust reverses its direction of flow in order to enter the second tube 208 via the venturi 290, a direction of exhaust flow inside the second tube 208 is opposite to the direction of exhaust flow inside the exhaust passage 204.

In addition, the second end 212 may block particulates and water particles 252 from entering the PM sensor assembly 202. Specifically, the outwardly flared up flanges of the second end may block the larger particulates, and hence reduce effects of impingement of particulates on the sensitive sensor element.

The exhaust flows through the second tube 208 along the path indicated by arrows 256. As indicated by the arrows 256, the direction of exhaust flow inside the straight portion 209 of the second tube 208 is opposite to direction of exhaust flow inside the exhaust passage. Then, exhaust flows from the second tube 208 towards the first tube 206 as indicated by arrow 257. Specifically, exhaust flows from the second to the first tube (arrow 257) in a direction orthogonal to each of exhaust flow inside the second tube 208, and exhaust flow inside the exhaust passage. In one example, the exhaust inside the straight portion 209 undergoes a 90° rotation to flow into the first tube 206.

The bottom seal 218 blocks exhaust flow from the lower chamber 238 to the upper chamber 236 except at the gap 224, thereby forcing exhaust in the lower chamber 238 to flow through a constriction formed at the gap 224. This leads to an additional increase in velocity of the exhaust gases as they flow from the lower chamber into the upper chamber 236 through the gap 224. The exhaust then flows from the gap 224 into the upper chamber 236. Once inside the upper chamber, exhaust flows through the perforations 216 (as indicated by arrow 257) on the baffle 217 towards the sensor element 214. Thus, exhaust flow undergoes another change in direction of flow (by 90°, for example) from an upwards direction (arrow 257) to flow towards the perforations (arrow 259). A length of the baffle may be equal to a length of the sensor element 214, for example. Herein, the sensor element 214 includes electrodes formed along a first surface of a substrate, and a heating element formed on an opposite surface of the substrate. A normal to the substrate of the sensor element 214 is orthogonal to a long axis of the baffle 217. In addition, the electrodes of the sensor element 214 are positioned closer to the plurality of perforations 216 and away from the outlet 228.

Typically, the sensor element 214 includes a pair of planar interdigitated electrodes forming a "comb" structure. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes are formed on a substrate that may be manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The spacing between the comb "tines" of the two electrodes may typically be in the range from 10 micrometers to 100 micrometers with the linewidth of each individual "tine" being about the same value, although the latter is not necessary.

A positive electrode of the pair of interdigitated electrodes of the sensor element 214 is connected with connecting wires 244 to a positive terminal of a voltage source 264 of an electric circuit 262. A negative electrode of the pair of interdigitated electrodes of the sensor element 214 is connected to a measurement device 270 via a connecting wire 246, and further connected to a negative terminal of the voltage source 264 of the electric circuit 262. The interconnecting wires 244 and 246, the voltage source 264 and the measurement device 270 are part of the electric circuit 262 and are housed outside the exhaust passage 204 (as one example, <1 meter away). Further, the voltage source 264 and the measurement device 270 of the electric circuit 262 may be controlled by a controller, such as controller 12 of FIG. 1, so that particulate matter collected at the sensor element 214 may be used for diagnosing leaks in a PF upstream of the exhaust gas sensor (e.g., DPF 102 in the embodiment of FIG. 1), for example. As such, the measurement device 270 may be any device capable of reading a resistance change across the electrodes, such as a voltmeter. As PM or soot particles get deposited between the electrodes of the sensor element 214, the resistance between the electrode pair may start to decrease, which is indicated by an increase in the current measured by the measurement device 270 for a fixed voltage (usually 45 V) of the voltage source 264. The controller 12 may be able to determine the resistance between the electrodes of the sensor element 214 as a function of electric current measured by the measurement device 270 and infer a corresponding PM or soot load on the electrodes of the sensor element 214. By monitoring the load on the sensor element 214, the exhaust soot load downstream of the DPF may be determined, and thereby used to diagnose and monitor the health and functioning of the DPF.

The sensor element 214 also includes a heating element (not labelled in FIG. 2B) that is integrated into the sensor substrate of the sensor element 214. In alternate embodiments, the sensor element 214 may not include a heating element. The heating element may comprise, but is not limited to, a temperature sensor, and a heater. Possible materials for the heater and the temperature sensor forming the heating element may include platinum, gold, palladium, and the like; and alloys, oxides, and combinations comprising at least one of the foregoing materials, with platinum/alumina, platinum/palladium, platinum, and palladium. The heating element may be used for regenerating the PM sensor assembly 202. Specifically, during conditions when the particulate matter load or soot load of the sensor element 214 is higher than a threshold, the heating element may be operated to burn accumulated soot particles from the surface of sensor element.

During PM sensor regeneration, the controller 12 may provide a voltage to a voltage source 266, which is needed for operating the heating element and is connected to the heating element via connecting wires 240 and 242. In addition, the controller may close a switch 268 for a threshold time to apply the voltage via the voltage source 266 to the heating element in order to raise the temperature of the heating element. Subsequently, when the sensor electrodes are sufficiently clean, the controller may open the switch 268 to stop heating the heating element. By intermittently regenerating the sensor element 214, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter.

After flowing towards the sensor element 214 where the soot particulates are captured across the electrodes, the exhaust flows towards the outlet 228 as indicated by arrow 258. Specifically, the portion of the exhaust gas flowing in the upper chamber 236 may exit via the outlet 228. The outlet 228 may be holes cut out on diametrically opposite surfaces of the first tube 206. Various other geometries of the outlet holes 228 may be possible without deviating from the scope of the disclosure. Other example geometries include trapezoidal, square, rectangular, and triangular apertures/ slits. In one example, the outlet 228 may include a trapezoidal slit that includes a long axis that is parallel to the central axis Y-Y' of the first tube 206. Two trapezoidal slits may be formed on the front wall and the back wall of the first tube 206. A length of the outlet 228 may be equal to a length L3 of the upper chamber 236. In some examples, the length of the outlet may be smaller than the length of the upper chamber 236. The trapezoidal outlet 228 may include a wider top and a narrower base. Exhaust exits the PM sensor assembly 202 through the outlet 228 (indicated by arrow 260) in a direction orthogonal to the direction of flow of exhaust inside the lower chamber 238. The advantage of using an L-shaped tube design with an outwardly opened up end serving as an inlet to the PM sensor assembly is that the opened up end blocks larger particulates from entering the assembly, and additionally serves to increase exhaust flow into the sensor assembly. In this way, the PM sensor assembly may be protected from impingement of water droplets and larger particulates and the PM sensor may be made more reliable. Overall, the functioning of the PM sensor to estimate the filtering capabilities of the DPF (and thereby to detect DPF leaks) may be increased and exhaust emissions compliance may be improved as particulates in the exhaust may be detected more accurately and reliably.

The example PM sensor assembly described so far includes a single L-shaped tube configured with inlet and outlet to direct exhaust into and out of the assembly as detailed in FIGS. 2A-2C. A second PM sensor assembly may be designed using the PM sensor assembly described thus far as an inner tube, and further positioning the inner tube within an outer L-shaped tube, as explained in FIGS. 3A and 3B.

Turning now to FIG. 3A, a schematic view 300 of an example embodiment of a particulate matter (PM) sensor assembly 302 (such as PM sensor 106 of FIG. 1, and PM sensor assembly 202 of FIGS. 2A-2C) is shown. The PM sensor assembly 302 may be configured to measure PM mass and/or concentration in the exhaust gas, and as such, may be coupled to an exhaust passage or pipe 304 (e.g., such as the exhaust passage 204 shown in FIGS. 2A-2C), upstream or downstream of a diesel particulate filter (such as DPF 102 shown in FIG. 1).

In the schematic view 300, the PM sensor assembly 302 is disposed inside the exhaust passage 304 with exhaust gases flowing (along X-axis) from downstream of the diesel particulate filter towards an exhaust tailpipe, as indicated by arrows 328. With reference to the PM sensor assembly 302, exhaust flows from an upstream side towards a downstream side of the assembly in the direction indicated by arrows 328. For example, the downstream side may be closer to an exhaust tailpipe. An axis system is shown comprising three axes, namely, an x-axis parallel to the horizontal direction, a y-axis parallel to the vertical direction, and a z-axis perpendicular to the x- and y-axes. The axis system shown on the view 300 may be used to describe the relative positioning of components of the PM sensor assembly 302. A "height/length" of the PM sensor assembly 302 and/or its components may be used to define the extent of the components along the y-axis. Similarly, a "length/diameter" of components of the PM sensor assembly 302 may be used to refer to the physical extent of the components along the x-axis. The physical extent of components along the z-axis may be referred to as a "width."

The PM sensor assembly 302 includes an inner, bent tube 306 positioned within an outer, bent tube 308 and separated from the outer tube 308 by a gap or space 310. There are no components in the gap 310. The inner tube 306 may be an example of the bent tube 203 described with reference to FIGS. 2A-2C, and may include all the details described with reference to the bent tube 203. Briefly, the inner tube 306 includes an L-shape hollow tube with a first closed end 318 coupling the inner tube 306 to the exhaust passage 304. In addition, the inner tube 306 includes a second outwardly flared up end 322 that serves as an inlet to the inner tube 306. Similar to the second end 212 of FIGS. 2A-2C, the second end 322 includes outwardly oriented flanges that form a venturi at the second end 322. The advantage of having a venturi formed at an end of the inner tube 306 is that a rate of exhaust flow into the inner tube 306 may be increased because of the Venturi effect described earlier.

The outer tube 308 is similar to the inner tube 306, and has an L-shaped tube assembly having a diameter D4. Similar to the inner tube 306, the outer tube 308 includes a first end 320 that is closed and further coupled to the exhaust passage 304 and includes a second end 324 that is open, and not coupled to the exhaust passage 304. However, the second end 324 of the outer tube 308 is not an outwardly flared end like the second end 322 of the inner tube 306. The second end 324 includes an open surface of uniform cross-section, unlike the second end 322 of the inner tube 306. Herein, the outer tube 308 has a uniform cross-section throughout the entire length of the outer tube 308. Thus, the vertical and horizontal portions (including the second end 324) of the outer tube 308 forming the L-shape geometry have the same diameter. The inner tube 306 may have a uniform cross-section (e.g., diameter D5) over the entire length, except at the second end 322. The inner tube 306 is positioned centrally within the outer tube 308, and further separated from the outer tube 308 by the gap 310. As such, the gap 310 results from the difference in diameters of the inner and the outer tubes. Thus, the gap 310 is mathematically written as (D4−D5)/2. The gap 310 is the annular space formed between the inner and the outer tubes, for example. The outer tube 308 additionally includes an inlet 326 formed upstream of the second end 322 of the inner tube 306. In one example, the inlet 326 may be located at the "elbow" or bent portion of the outer tube 308. The inlet 326 may be an elliptical hole configured to direct exhaust into the PM sensor assembly 302 in a direction parallel to the direction of flow of exhaust inside the exhaust passage 304. In some examples, the inlet 326 may include a plurality of holes formed along the upstream surface of the outer tube 308. The purpose of the inlet 326 is to allow exhaust to flow into the gap 310 as shown in FIG. 3B.

Turning to FIG. 3B, schematic view 350 shows exhaust flow through the PM sensor assembly 302. As such, components previously introduced in FIG. 3A are numbered similarly in FIG. 3B. The view 350 depicts exhaust flowing into the PM sensor assembly 302 via the inlet 326.

Exhaust enters the PM sensor assembly 302 through the inlet 326 in a direction parallel to the direction of exhaust flowing inside the exhaust passage 304 (arrow 328). Specifically, exhaust enters the gap 310 formed between the inner tube 306 and the outer tube 308 (arrow 352). As such, larger particulates 360 may flow into the gap 310, and flow out of the assembly 302 via the second end 324 of the outer tube 308. Further, large particulates and/or water droplets (as shown by circles 360) may continue flowing in the horizontal direction inside the gap 310 without entering the inner tube 306. The greater momentum of the large particulates and/or water droplets inhibits a turning and/or direction change of the large particulates and/or water droplets into the opening formed at the second end 322 of the inner tube 306. Some exhaust may enter the assembly 302 via the second end 324 of the outer tube. However, the amount of exhaust entering via the inlet 326 from the upstream side is larger than the amount of exhaust entering via the second end 324 that is at the downstream side.

The exhaust inside the gap 310 between the inner and the outer tubes may encounter the venturi opening formed in the second end 322 of the inner tube 306. As explained with reference to FIGS. 2A-2C, exhaust flows into the second end 322 of the inner tube by reversing its direction of flow. Thus, exhaust entering the inner tube 306 flows in a direction opposite to each of exhaust flow inside the gap, and the exhaust flow inside the exhaust passage 304. By positioning the venturi opening at the second end 322 of the inner tube, the velocity of the exhaust is increased when exhaust flows from the higher cross-section opening towards the smaller cross-section of the inner tube 306. As a result, exhaust flowing into the inner tube 306 has a higher flow rate than exhaust flowing inside the exhaust passage, and exhaust flowing inside the gap 310, for example. This in turn increases the exhaust PM flowing into the inner tube 306, thus causing more exhaust PM to flow towards the sensor element 312 of the assembly 302 and be deposited across the electrodes. Subsequently, the sensitivity of the sensor assembly is increased.

Once inside the inner tube, the exhaust flows opposite (arrow 353) to the direction of flow inside the exhaust passage as explained previously with reference to FIG. 2B. In addition, the exhaust continues to flow upwards against gravity (arrow 354) in the vertical portion of the inner tube 306 towards the plurality of perforations 316. In some example embodiments, the inner tube 306 may include a bottom seal, and a baffle with plurality of perforations configured to guide the exhaust inside the inner tube 306 towards a sensor element 312 positioned closer to the perforations (similar to the bent tube 203 of FIGS. 2A-2C). In other example embodiments, the inner tube 306 may include a plurality of perforations 316 formed along a top portion 314 of the inner tube 306. Specifically, the plurality of perforations 316 may be formed along the top portion 314 of the downstream sidewall of the inner tube 306 that is downstream of the inlet 326 of the outer tube 308. Herein, the top portion 314 may extend to a certain length from the top end 318 of the inner tube 306 along the downstream sidewall of the inner tube 306. Additionally, the plurality of perforations may be configured to direct the exhaust from inside the inner tube 306 towards the gap 310 between the inner and the outer tubes. A sensor element 312 may be positioned downstream of the plurality of perforations within the gap 310 to collect exhaust PM as described in FIGS. 4A-4D.

FIG. 4A shows an exterior side perspective view 400 of PM sensor assembly 302. FIG. 4B shows a top-down view 425 of PM sensor assembly 302. Portions of the PM sensor assembly 302 in the exterior side perspective view 400 are transparent, exposing an interior of the PM sensor assembly 302, including sensor element 312 and inner tube 306. FIGS. 4C and 4D depict detailed illustrations of the sensor element 312.

Turning now to FIG. 4A, view 400 shows the plurality of perforations 316 formed on the portion 314 of the inner tube 306. Specifically, the plurality of perforations 316 includes a uniform array of holes covering the portion 314. In the view 400, five columns and eight rows of equally spaced circular holes are shown as a non-limiting example of the plurality of perforations 316. Various other geometry, shape, and distribution of the holes are possible without deviating from the scope of the disclosure. In one example, the plurality of perforations 316 may be spread out over an area of the downstream sidewall of the inner tube 306 that matches the surface area of the sensor element 312. The advantage of having the plurality of perforations 316 spread out over the portion 314 is that the exhaust flowing towards electrodes 402 of the sensor element 312 is more evenly distributed. This results in a more reliable output from the sensor element 312.

Exhaust flows out of the inner tube 306, via the plurality of perforations 316, and into the annular space or gap 310 between the outer tube 308 and the inner tube 306. Exhaust exits the inner tube 306 via the perforations 316 in a radially outward direction (arrow 426) toward the electrodes 402 of the sensor element 312.

Turning now to FIG. 4B, top-down view 425 shows the sensor element 312 positioned in the gap 310 between the inner tube 306 and the outer tube 308. Particulates in the exhaust may be deposited onto a first surface 427 having the electrodes 402. In one example, the sensor element 312 may include a planar substrate having interdigitated positive and negative electrodes formed on a surface of the sensor element, the surface facing towards the plurality of perforations 316. The planar substrates and the interdigitated electrodes may include all the details previously described with reference to the sensor element 214 of FIG. 2B.

In another example, instead of being planar, the substrate 430 of the sensor element 312 may be curved (while the details of the substrate and the electrodes remain similar to those previously described in FIG. 2B). It may be advantageous to include a curved sensor element in the gap 310 between the inner tube 306 and the outer tube 308, as the surface area available for capturing the incoming soot particles may be larger than a planar sensor element, for example. The curvature of the substrate 430 may depend on the curvature (or radius) of each of the inner tube 306, and outer tube 308. In the top view 425, the curved substrate 430 is represented as an arc, with a radius R6 that is dependent on each of the radius R4 of the outer tube 308, and radius R5 of the inner tube 306. Herein, a center C of each of the inner tube, the outer tube, and the curved substrate may be coincident. In one example, the curved substrate may be positioned midway inside the gap 310 between the inner and the outer tubes. In such an example, R6 may be equal to (R4+R5)/2. Said another way, the curved substrate 430 may be positioned in the middle of the gap 310, at a distance given by (D4−D5)/4 or (R4−R5)/2. In some other examples, the curved substrate 430 may be placed closer to the inner tube (or farther from the outer tube) or closer to the outer tube (farther from the inner tube) instead of in the middle. However, the curved substrate 430 may be positioned inside the gap 310, and thus not protruding out of the PM sensor assembly 302.

As shown in view 425, the first surface 427 of the sensor substrate 430 faces an exterior surface of the inner tube 306 and a second surface 429 faces an interior surface of the outer tube 308. The second surface 429 is diametrically opposite to first surface 427, and faces in the opposite direction towards the interior surface of the outer tube 308. The particulates may accumulate onto or between individual electrodes of the electrodes 402. However, exhaust gas entering the gap 310 from the inner tube 306 may not flow directly into the heating element without flowing around the sensor substrate 430, in some examples.

Turning now to FIG. 4C, a head-on view 460 of the first surface 427 of the sensor substrate 430 is shown. The first surface 427 of the sensor element 312 comprises a pair of interdigitated electrodes 404 and 406. The electrodes 404 and 406 are fixed to the sensor substrate 430, which is configured to capture soot from exhaust gas flowing out of the perforations 316 of the inner tube 306. The pair of electrodes 404 and 406 traverses a portion of the curvature of the sensor substrate 430 such that the electrodes 404 and 406 are located directly across from the perforations 316. Herein, the electrodes 404 and 406 may include a curvature that is equal to the curvature of the substrate 430. Soot (e.g., particulate matter) may accumulate between the pair of interdigitated electrodes 404 and 406, where soot electrically couples (e.g., bridges) the electrodes 404 and 406 upon reaching a threshold soot load. FIG. 4D shows the second surface 429 of the sensor element 312 having the heating element 428 physically coupled to the sensor substrate 216 at the second surface 429. The second surface 429 is opposite the first surface 427 such that the heating element 428 faces an opposite direction that the pair of electrodes 404 and 406 face. Specifically, the first surface 427 faces the perforations 316 on an exterior surface of the inner tube 306 while the second surface 429 faces an interior surface of the outer tube 308.

The electrodes 404 and 406 are connected via connecting wires to positive and negative terminals, respectively, of a voltage source 464 of an electric circuit 462. The details of the electric circuit 462, and the corresponding circuitry is the same as the details of the electric circuit 262 described with reference to FIG. 2B. Briefly, the positive electrode 404 is connected with connecting wires 470 to a positive terminal of a voltage source 464 of the electric circuit 462. The negative electrode 406 is connected to a measurement device 466 via the connecting wire 468, and further connected to a negative terminal of the voltage source 464 of the electric circuit 462. The voltage source 464 and the measurement device 466 of the electric circuit 462 may be controlled by a controller, such as controller 12 of FIG. 1, so that particulate matter collected at the sensor element 312 may be used for diagnosing leaks in a PF upstream of the exhaust gas sensor (e.g., DPF 102 in the embodiment of FIG. 1), for example. The controller 12 may be able to determine the resistance between the electrodes of the sensor element 312 as a function of electric current measured by the measurement device 466 and infer a corresponding PM or soot load on the electrodes of the sensor element 312. By monitoring the load on the sensor element 312, the exhaust soot load downstream of the DPF may be determined, and thereby used to diagnose and monitor the health and functioning of the DPF.

The sensor element 312 also includes the heating element 428 that is formed on the second, opposite surface 429. Turning to FIG. 4D, the heating element 428 may comprise, but is not limited to, a temperature sensor, and a heater. Possible materials for the heater and the temperature sensor forming the heating element may include platinum, gold, palladium, and the like; and alloys, oxides, and combinations comprising at least one of the foregoing materials, with platinum/alumina, platinum/palladium, platinum, and palladium. The heating element 428 may be used for regenerating the PM sensor assembly 302. Specifically, during conditions when the particulate matter load or soot load of the sensor element 312 is higher than a threshold, the heating element may be operated to burn accumulated soot particles from the surface of sensor element.

During PM sensor regeneration, the controller 12 may provide a voltage to a voltage source 484, which is needed for operating the heating element and is connected to the heating element via connecting wires 486 and 488. In addition, the controller may close a switch 482 for a threshold time to apply the voltage via the voltage source 484 to the heating element 428 in order to raise the temperature of the heating element. Subsequently, when the sensor electrodes are sufficiently clean, the controller may open the switch 482 to stop heating the heating element. By intermittently regenerating the sensor element 312, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter.

After flowing towards the sensor element 312 where the soot particulates are captured across the electrodes, the exhaust flows towards the second end 324 of the outer tube 308 as shown in FIG. 3B. Returning to FIG. 3B, the exhaust spirals in the gap 310 between the inner and the outer tubes, and flows towards the second open end 324 of the outer tube 308. Exhaust exits the PM sensor assembly 302 via the second end 324 of the outer tube 308 parallel to the direction of exhaust flow through the exhaust passage 304. The exhaust gas flows through the inner tube that is adapted to limit large particulates and/or water droplets from entering the PM sensor assembly. This may improve diagnostic measurements of a PF upstream of the PM sensor assembly due to a uniform particulate deposition onto the sensor substrate.

In this way, the system of FIGS. 1-4C enables an example particulate matter (PM) assembly comprising: a bent tube having a first closed end and a second outwardly flared end, a plurality of perforations formed proximate to the first end, and a sensor element positioned facing towards the plurality of perforations, the sensor element located upstream of the second end. Additionally or alternatively, the bent tube may include a first tube coupled to a second, orthogonal tube forming an L-shape, the first end of the bent tube formed at an end of the first tube, and the second end of the bent tube formed at an end of the second tube. Additionally or alternatively, the first end may be directly coupled to an exhaust passage, the first tube having a straight portion of uniform cross-section. Additionally or alternatively, the second tube may include a straight portion of uniform cross-section coupled to the second end of the bent tube, the second end having an outwardly angled portion of increasing cross-section positioned inside the exhaust passage such that exhaust inside the exhaust passage reverses a direction of flow to enter the PM sensor assembly through the second end. Additionally or alternatively, the first tubes may comprise a bottom seal at a first distance from the first end, the bottom seal coupled to a first side surface of the first tube and at a first gap from a second, opposite side surface of the first tube, the bottom seal having a length that is smaller than a diameter of the first tube, a rectangular baffle having the plurality of perforations, an axis of the baffle parallel to an axis of the sensor element wherein the sensor element is at a second gap from the baffle, and an outlet having an axis parallel to the axis of the sensor element. Additionally or alternatively, the bent tube may be an inner tube positioned within an outer, L-shaped, tube and separated from the outer tube by a space, the outer tube having a third, closed end coupled to an exhaust passage, and a fourth, open end positioned inside the exhaust passage, the fourth open end proximate to the second end of the inner tube. Additionally or alternatively, the outer tube may comprise an inlet upstream of the sensor element configured to direct exhaust from the exhaust passage first into the space between outer tube and the inner tube in a direction parallel to exhaust flow inside the exhaust passage. Additionally or alternatively, the plurality of perforations may be formed on a downstream side of the inner tube, and wherein the sensor element is positioned in the space between the inner tube and the outer tube facing towards the plurality of perforations. Additionally or alternatively, the sensor element may include interdigitated electrodes formed on a curved substrate. Additionally or alternatively, the assembly may further comprise a heating element coupled to the sensor element, and a controller with computer readable instructions stored on non-transitory memory for: during exhaust flow, applying a first voltage to electrodes of the sensor element to accumulate exhaust particulate matter in the exhaust across the electrodes, estimating a load on the assembly based on a current generated across the electrodes of the sensor element, and responsive to the load being higher than a threshold, applying a second, different voltage to the heating element to regenerate the sensor element.

Yet another example particulate matter (PM) sensor assembly may include a protection tube having a vertical portion fluidically coupled to a horizontal portion, the vertical portion coupled to an exhaust pipe, and the horizontal portion having a venturi, a plurality of orifices formed within the vertical portion, and a sensor element positioned within the vertical portion, the sensor element upstream of the venturi, and a normal to the sensor element orthogonal to a surface having the plurality of orifices. Additionally or alternatively, the venturi may couple the horizontal portion to an opened up end, the opened up end having an outwardly increasing cross-section that directs exhaust from into the horizontal portion and then towards the sensor element through the plurality of orifices and out of the assembly via a trapezoidal opening formed on the vertical portion, wherein the plurality of orifices are formed on a rectangular baffle positioned inside the vertical portion between a top end of the vertical portion and a bottom seal, the bottom located at a distance from the top end of the vertical portion, and wherein the sensor element includes interdigitated electrodes formed on a planar substrate located inside the vertical portion between the top end and the bottom seal. Additionally or alternatively, the protection tube may be positioned within an outer tube and separated from the outer tube by a space, and wherein the outer tube may include a hole formed at an elbow region of the protection tube, the hole configured to direct exhaust from the exhaust pipe first into the space, and then from the space towards the venturi formed on the inner tube towards the sensor element through the plurality of orifices, and subsequently out of the assembly through an open end of the outer tube, and wherein the plurality of orifices may be formed on a region of the vertical portion upstream of the sensor element, and wherein the sensor element includes interdigitated electrodes formed on a curved substrate, the sensor element placed inside the space between the protection tube and the outer tube.

FIGS. 1-4D show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 5:
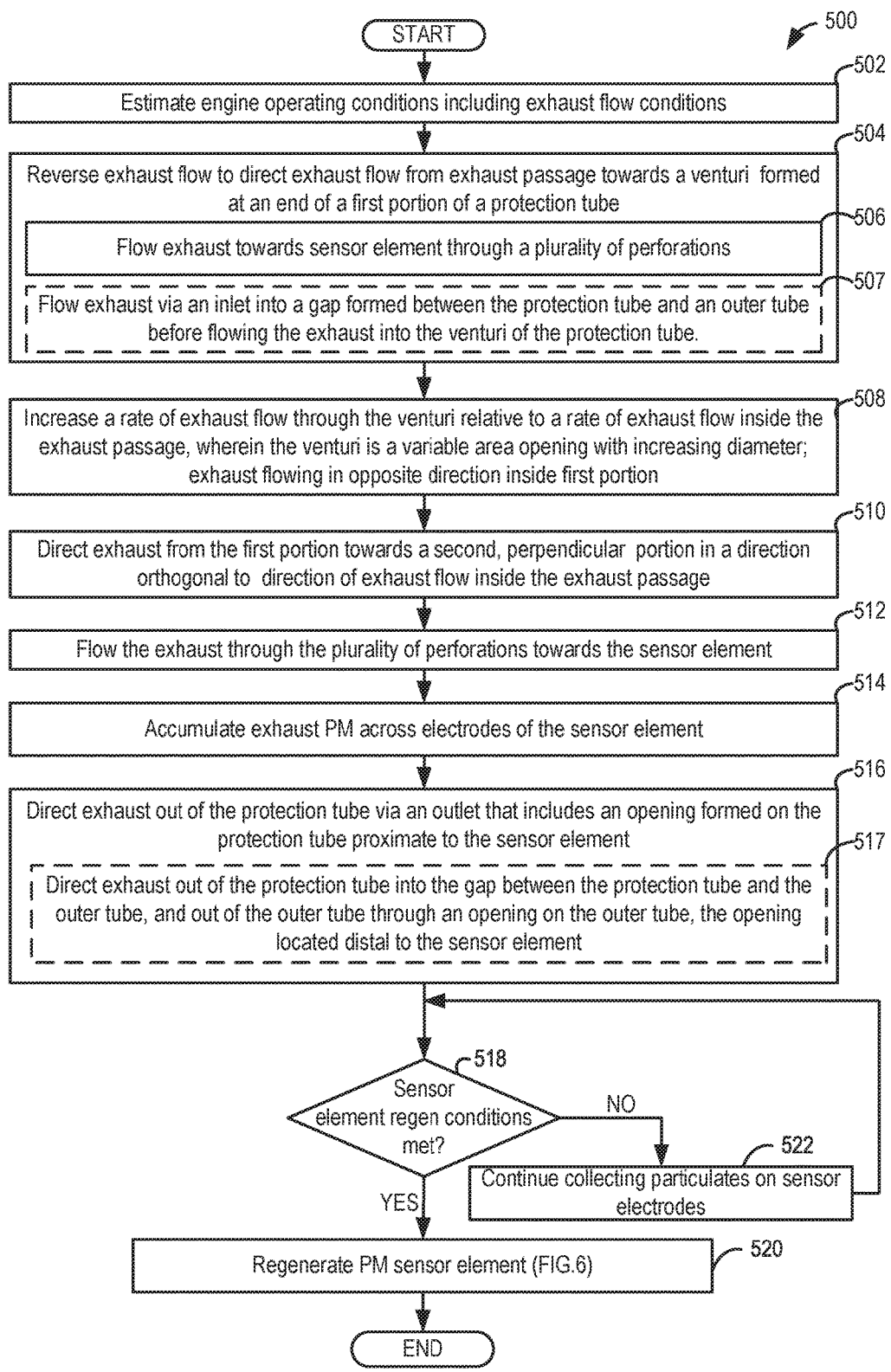
FIG. 5 shows a flow chart depicting an example method for accumulating particulates in the exhaust flow across the sensor element positioned within the protection tube of the PM sensor assembly.

Turning now to FIG. 5, an example method 500 for accumulating particulates in the exhaust flow across sensor electrodes positioned within the PM sensor assembly (such as a PM sensor 106 shown at FIG. 1, and/or PM sensor assembly 202 of FIGS. 2A and 2B, PM sensor assembly 302 of FIGS. 3A-3B and 4A-4D, for example) is shown. Specifically, the particulates in the exhaust flow may be directed into a venturi-like inlet formed at an end of a bent tube, and further directed through a plurality of perforations towards a sensor element. The particles may be accumulated across interdigitated electrodes formed on the sensor substrate (planar or curved) of the sensor element.

Instructions for carrying out method 500 and the rest of the methods included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 502, method 500 includes determining and/or estimating engine-operating conditions. Engine operating conditions determined may include, for example, engine speed, engine load, driver torque demand, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

Method 500 proceeds to 504 where the method includes reversing an exhaust flow to direct exhaust from inside an exhaust passage towards a venturi formed at an end of a first portion of a protection tube. Specifically, the venturi is formed via the coupling of a region of increasing cross-section to a region with uniform cross-section. By forming the venturi at the downstream side of an L-shaped protection tube where the static pressure is higher, exhaust inside the exhaust passage is forced to reverse its direction of flow in order to enter the PM sensor assembly. In one example configuration, the venturi is formed at the end of a single L-shaped protection tube (such as bent tube 203 of FIGS. 2A-2B), and reversing the exhaust flow includes flowing the exhaust inside the L-shaped tube in a direction opposite to direction of exhaust flow inside the exhaust passage towards a sensor element through a plurality of perforations at 506. As such, the L-shaped tube includes a first, horizontal portion fluidically coupled to a second, vertical portion. Herein, the venturi is formed at the end of the first portion, and the sensor element, and the plurality of perforations are located inside the second portion, upstream of the venturi.

In another example, the L-shaped tube having the venturi at the downstream side may be an inner protection tube positioned within an outer, L-shaped protection tube (such as PM sensor assembly 302 of FIGS. 3A-4D), and separated from the outer tube by a gap. Herein, the inner tube may be entirely inside the outer tube, with no parts projecting outside of the outer tube. In addition, only the inner tube may include a venturi as an opening; the outer tube may include an opening formed on an upstream side that may serve as an opening to the outer tube. As a result, the venturi is formed at an end of the first, horizontal portion of the inner tube, and the inlet is formed at the intersection of the horizontal and vertical portions of the outer tube, facing towards the incoming exhaust. Herein reversing an exhaust flow may include, at 507, flowing the exhaust through the inlet into the gap between the inner and the outer tubes, and then flowing the exhaust from the gap towards the venturi formed on the inner tube.

Method 500 then proceeds to 508. At 508, method 500 includes increasing a rate of exhaust flow through the venturi relative to a rate of exhaust flow inside the exhaust passage. Herein, the venturi is a variable area opening formed by coupling a region of increasing cross-section with a region of uniform cross-section. As such, when exhaust first flows from the region of increasing cross-section towards the region of uniform cross-section, the exhaust encounters a constriction. As a result, the velocity of exhaust flow is increased. Thus, by using the venturi design as the opening of the L-shaped tube, the exhaust flow inside the L-shaped tube is increased relative to the exhaust flow inside the exhaust passage. In the example configuration wherein the venturi is formed on the inner tube, the flow inside the inner tube is higher than the flow inside the exhaust passage as well as flow inside the gap between the inner and the outer tubes.

Method 500 proceeds to 510. At 510, method 500 includes directing exhaust from the first, horizontal portion towards the second, vertical portion, in a direction orthogonal to the direction of exhaust flow inside the exhaust passage. The geometry or structure of the L-shaped tube having vertical and horizontal portions coupled to one forces the exhaust inside the horizontal portion to move upward (against gravity) towards the second portion.

Method 500 proceeds to 512. At 512, method 500 includes flowing the exhaust through a plurality of perforations towards the sensor element, both of which are located inside the second portion of the L-shaped protection tube. In the example of a single protection tube, the exhaust inside the second portion may be directed towards another constriction, before reaching the plurality of perforations. As an example, a bottom seal may extend horizontally form a downstream wall of the protection tube, but may not extend all the way to the opposite upstream wall. There may be a gap or space between the end of the bottom seal and the upstream wall. Exhaust inside the second portion is now forced to flow into the space before reaching the plurality of perforations. The plurality of perforations may be formed on a rectangular baffle, a long axis of the baffle being parallel to a central axis of the second portion. Further, a sensor element may be positioned adjacent to the rectangular baffle. The sensor element may additionally be oriented parallel to the central axis of the second portion of the protection tube. The sensor element may include electrodes that are formed along a first surface closer to the plurality of perforations. Herein, the electrodes may be extend in an orthogonal direction relative to the central axis of the second portion of the protection tube.

In the example configuration where the protection tube is an inner tube positioned inside the outer tube, method 500 may optionally include flowing the exhaust from the second portion of the inner tube towards a plurality of perforations formed on a downstream wall of the inner tube. In addition, a curved sensor may be positioned in the gap between the inner and outer tubes, with the sensor electrodes facing towards the plurality of perforations. Exhaust flowing out of the plurality of perforations is directed towards the electrodes of the sensor element.

Method 500 proceeds to 514. At 514, method 500 includes accumulating exhaust PM across the electrodes of the sensor element. As described previously, the sensor element including interdigitated electrodes is positioned at a distance from the perforations. In one example, the sensor element may include a planar substrate with planar interdigitated electrodes formed on a first surface of the substrate. In another example, the sensor element may include a curved substrate having curved interdigitated electrodes formed on a first surface of the substrate. For both the planar element and the curved element, the first surface of the substrate is closer to a surface including the perforations. As explained previously, the electrodes may include interdigitated electrodes. The positive electrodes are connected to the positive terminal of a voltage supply and the negative electrodes are connected to a measurement device and then to the negative terminal of the voltage supply. When the controller applies a voltage to the sensor electrodes, particulates inside the region enclosed between the plane of the perforations, and the first surface of the sensor element may experience a strong electric field, enabling them to be accumulated between the electrodes. As particulates accumulate across the electrodes, the controller may receive a signal from a measurement device. In one example, the signal may be a change in current/resistance across the electrodes from the measurement device (such as ammeter, or ohmmeter). Based on the signal received from the measurement device, the controller may determine a load on the sensor electrodes. When particulates accumulate on the surface of the sensor electrodes, the resistance of the electrodes starts decreasing and a current measured by the measurement device starts to increase. The controller may be able to deduce a load on the sensor electrodes based on the current measured across the electrodes. The controller may alternatively determine the load based on a calculation using a look-up table with the input being current/resistance between the electrodes. Method 500 then proceeds to 516.

At 516, method 500 includes directing the exhaust out of the protection tube via an outlet that includes an opening formed on the protection tube. In one example, the outlet may be trapezoidal opening formed on the second portion of the protection tube proximate to the sensor element.

In the example where the protection tube includes the inner and the outer tubes, the method includes directing the exhaust out of the inner protection tube into the gap between the inner tube and the outer tube at 517. Additionally, exhaust is directed out of the PM sensor assembly through an opening formed on the outer tube. Herein, the opening may be formed at an end of a horizontal portion of the outer tube. The end may be located downstream of the sensor element, and further distal to the sensor element. Method 500 proceeds to 518.

At 518, method 500 includes intermittently checking if the sensor element has met the regeneration conditions. Specifically, when the soot load on the sensor element is greater than the threshold, or when a resistance of the sensor element (adjusted for temperature) drops to a threshold resistance, or when a current of the sensor element is greater than a threshold current, sensor regeneration conditions may be considered met. In some examples, if a threshold time has elapsed since an immediately previous sensor regeneration, regeneration condition may be considered met. The sensor element may require regeneration to enable further PM detection.

Figure 6:
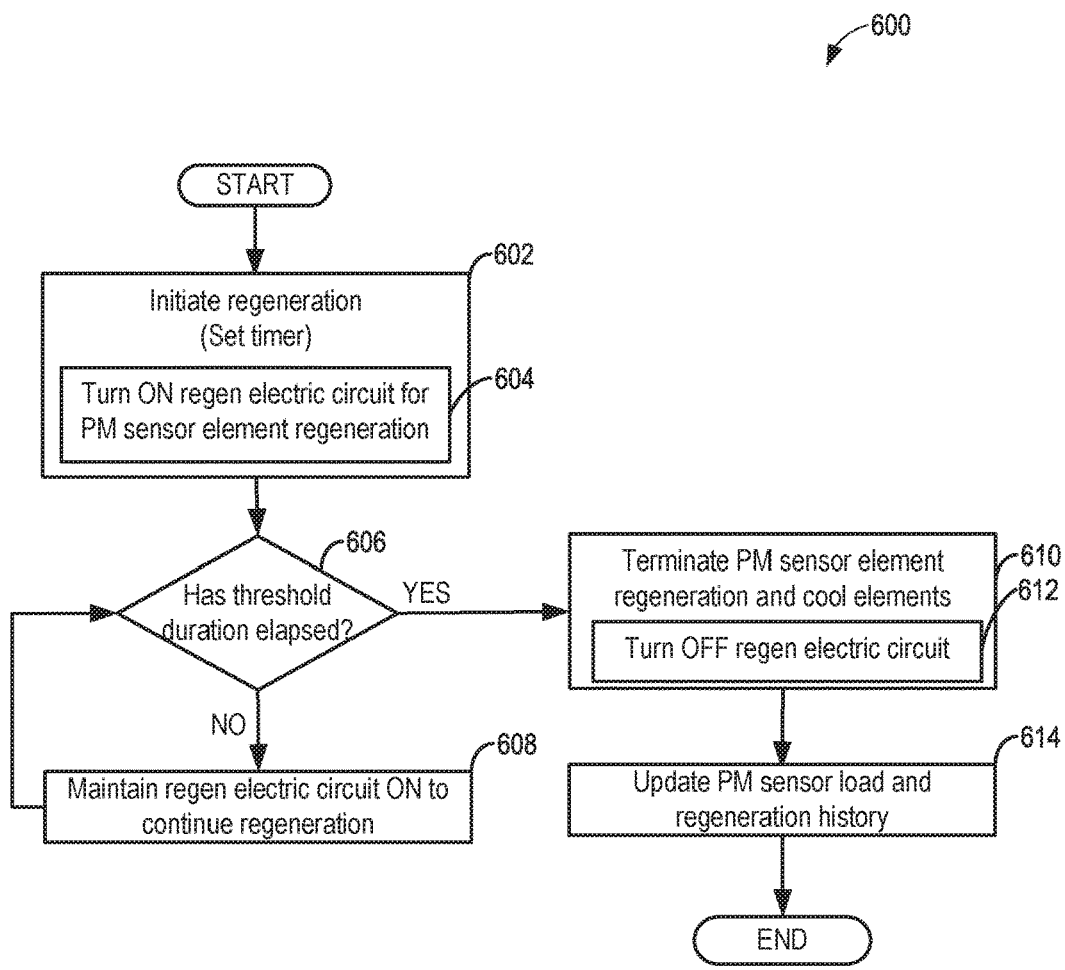
FIG. 6 is a flow chart depicting an example method for regenerating the sensor element of the PM sensor assembly.

If regeneration conditions are met (e.g., "YES" at 518), then method 500 proceeds to 520 where the sensor element may be regenerated by performing a method described in FIG. 6. Briefly, regeneration of the sensor element may be initiated by heating up the sensor. The sensor may be heated by actuating a heating element formed on a different surface of the sensor element that is opposite to the surface including the electrodes, for example. Herein, the controller may close the switch in a regeneration circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes. Method 500 ends. However, if PM sensor regeneration conditions are not met (e.g., "NO" at 518), then method proceeds to 522 where the particulates may continue to be collected on the sensor electrodes and the method returns to 518.

Thus, an example method includes reversing exhaust flow to direct exhaust from inside an exhaust passage towards a venturi, the venturi formed at an end of a first portion of a protection tube, and flowing the exhaust from the venturi towards a sensor element through a plurality of perforations, the sensor element positioned within a second portion of the protection tube upstream of the venturi. Additionally or alternatively, the method further comprises increasing a rate of exhaust flow through the venturi relative to the rate of exhaust flow inside the exhaust passage, wherein the venturi is a variable area opening formed by coupling a region of with increasing cross-section with a region of constant cross-section. Additionally or alternatively, the flowing includes flowing the exhaust from the venturi into the first portion of the protection tube in a direction opposite to a direction of exhaust flow inside the exhaust passage, directing the exhaust from the first portion into a second portion of the protection tube in a direction orthogonal to the direction of exhaust flow inside the exhaust passage, the second portion fluidically coupled to and orthogonal to the first portion, flowing the exhaust through the plurality of perforations towards the sensor element, and directing the exhaust out of the protection tube through an outlet. Additionally or alternatively, the plurality of perforations may be formed on a baffle, the baffle coupled to a bottom plate, the bottom plate and the baffle positioned within the second portion, and wherein the sensor element may be coupled to the bottom plate and faces towards the plurality of perforations. Additionally or alternatively, the protection tube may be an inner tube positioned within an outer tube. Additionally or alternatively, the flowing further comprises includes flowing exhaust into a gap between the inner tube and the outer tube through an inlet formed on the outer tube, the inlet upstream of the venturi and the sensor element before flowing the exhaust into the venturi. Additionally or alternatively, the plurality of perforations may be formed on each of a surface of the inner tube, the surface upstream of the venturi, and the surface downstream of the sensor element, and wherein the sensor element is curved and positioned in the gap between the inner and the outer tube.

Turning now to FIG. 6, a method 600 for regenerating the PM sensor (such as a PM sensor 106 shown at FIG. 1, and/or PM sensor assembly 202 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 602, regeneration of the PM sensor may be initiated and the PM sensor may be regenerated by heating up the sensor at 604. The controller may actuate a heating element until the soot load of the sensor has been sufficiently reduced by oxidation of the carbon particles between the electrodes. The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
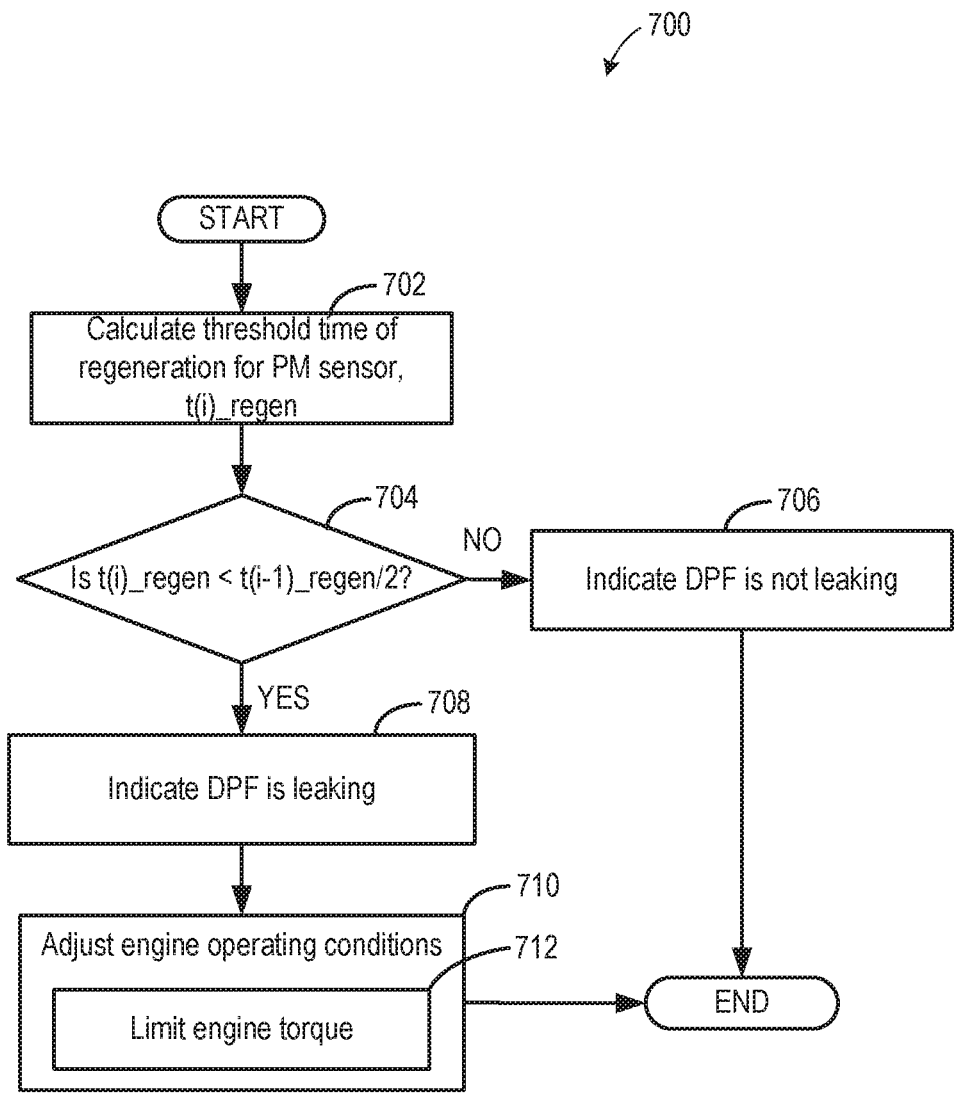
FIG. 7 shows a flow chart depicting an example method for diagnosing leaks in a particulate filter positioned upstream of the PM sensor assembly.
Figure 8:
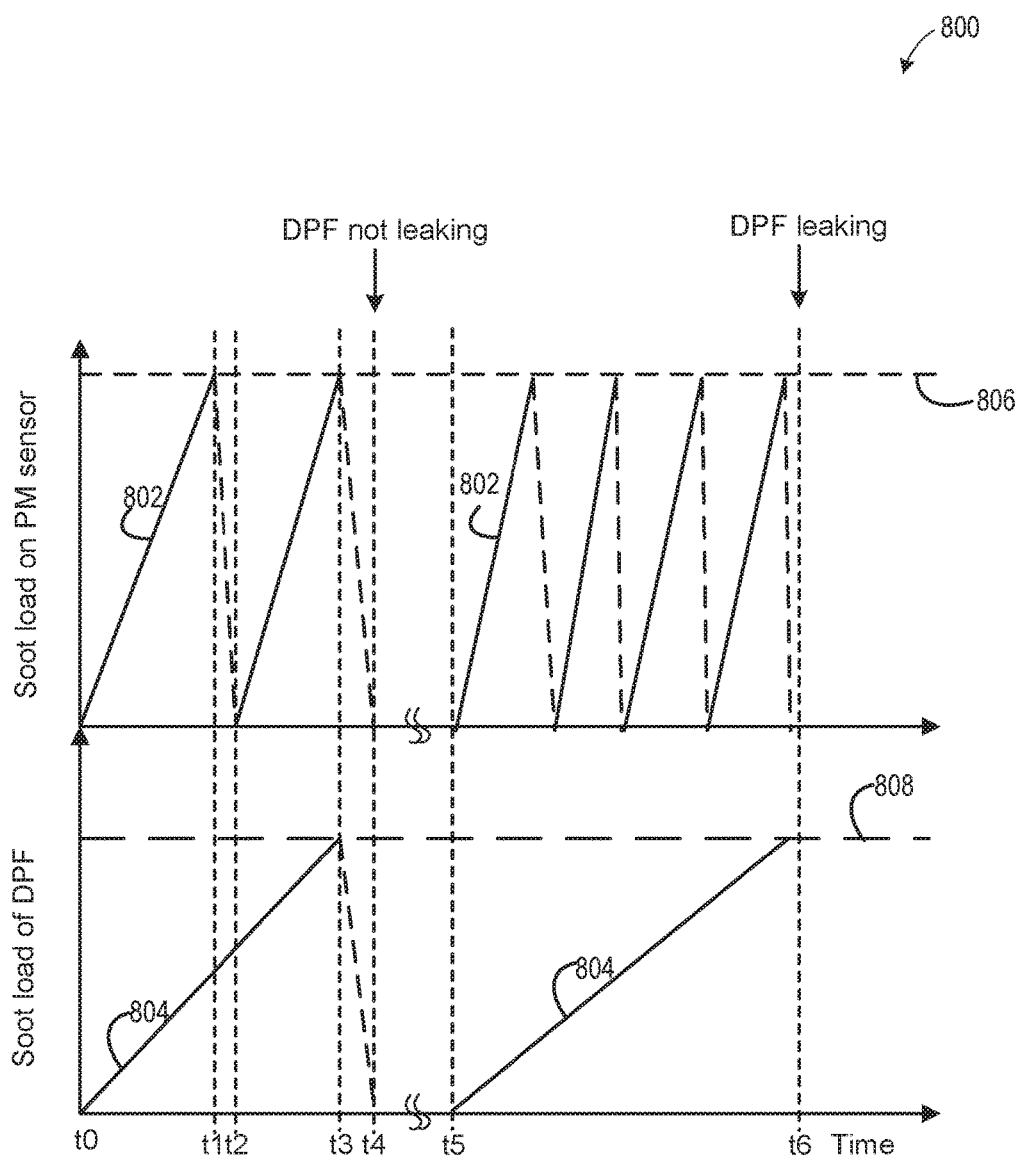
FIG. 8 shows an example relationship between a soot load on the PM sensor assembly, and a soot load on a particulate filter positioned upstream of the PM sensor assembly.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and DPF.

The first plot of FIG. 8 shows a soot load on the PM sensor. As previously described, PM gets deposited across the positive and negative electrodes formed on a plate that is positioned inside a stepped assembly. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, as PM continues to accumulate, the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may require regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804) reaches the threshold soot load for DPF regeneration (marker 808). Between t3 and t4, the DPF may be regenerated to burn off the soot deposited on the DPF. Further, at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore, at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended. The technical effect of forming a venturi at the downstream side of the L-shaped protection tube is that the velocity of the exhaust increases as it passes through the venturi in accord with the Venturi effect. By increasing the exhaust flow speed into the PM sensor assembly, soot particles in the exhaust may be captured across the electrodes of the sensor element at an increased rate. Thus, the output of the PM sensor assembly may reliably indicate the amount of soot particles flowing through an upstream particulate filter. In this way, the functioning of the PM sensor assembly to estimate the filtering capabilities of the DPF (and thereby to detect DPF leaks) may be increased. In addition, as the exhaust is streamed from the downstream side of the L-shaped protection tube, water droplets and/or larger particulates may continue to flow past the venturi without redirecting their flow direction to enter the venturi. Therefore, the sensor element may be protected from impingement of water droplets and larger particulates. Overall, the functioning of the PM sensor assembly may be improved and PM sensor output may be more reliable.

The systems and methods described above provide for a particulate matter sensor (PM) assembly, comprising a bent tube having a first closed end and a second outwardly flared end, a plurality of perforations formed proximate to the first end, and a sensor element positioned facing towards the plurality of perforations, the sensor element located upstream of the second end. In a first example of the particulate matter sensor assembly, the sensor may additionally or alternatively include wherein the bent tube includes a first tube coupled to a second, orthogonal tube forming an L-shape, the first end of the bent tube formed at an end of the first tube, and the second end of the bent tube formed at an end of the second tube. A second example of the particulate matter sensor optionally includes the first example and further includes wherein the first end is directly coupled to an exhaust passage, the first tube having a straight portion of uniform cross-section. A third example of the particulate matter sensor optionally includes one or more of the first and the second examples, and further includes wherein the second tube includes a straight portion of uniform cross-section coupled to the second end of the bent tube, the second end having an outwardly angled portion of increasing cross-section positioned inside the exhaust passage such that exhaust inside the exhaust passage reverses a direction of flow to enter the PM sensor assembly through the second end. A fourth example of the particulate matter sensor optionally includes one or more of the first through the third examples, and further includes wherein the first tubes comprises a bottom seal at a first distance from the first end, the bottom seal coupled to a first side surface of the first tube and at a first gap from a second, opposite side surface of the first tube, the bottom seal having a length that is smaller than a diameter of the first tube, a rectangular baffle having the plurality of perforations, a long axis of the baffle parallel to a long axis of the sensor element wherein the sensor element is at a second gap from the baffle, and an outlet having a long axis parallel to the long axis of the sensor element. A fifth example of the particulate matter sensor optionally includes one or more of the first through the fourth examples, and further includes wherein the bent tube is an inner tube positioned within an outer, L-shaped, tube and separated from the outer tube by a space, the outer tube having a third, closed end coupled to an exhaust passage, and a fourth, open end positioned inside the exhaust passage, the fourth open end proximate to the second end of the inner tube. A sixth example of the particulate matter sensor optionally includes one or more of the first through the fifth examples, and further includes wherein the outer tube comprises an inlet upstream of the sensor element configured to direct exhaust from the exhaust passage first into the space between outer tube and the inner tube in a direction parallel to exhaust flow inside the exhaust passage. A seventh example of the particulate matter sensor optionally includes one or more of the first through the sixth examples, and further includes wherein the plurality of perforations are formed on a downstream side of the inner tube, and wherein the sensor element is positioned in the space between the inner tube and the outer tube facing towards the plurality of perforations. An eighth example of the particulate matter sensor optionally includes one or more of the first through the seventh examples, and further includes wherein the sensor element includes interdigitated electrodes formed on a curved substrate. A ninth example of the particulate matter sensor optionally includes one or more of the first through the eighth examples, and further includes a heating element coupled to the sensor element, and a controller with computer readable instructions stored on non-transitory memory for: during exhaust flow, applying a first voltage to electrodes of the sensor element to accumulate exhaust particulate matter in the exhaust flow across the electrodes, estimating a load on the assembly based on a current generated across the electrodes of the sensor element, and responsive to the load being higher than a threshold, applying a second, different voltage to the heating element to regenerate the sensor element.

The systems and methods described above also provide for a method, the method comprising reversing exhaust flow to direct exhaust from inside an exhaust passage towards a venturi, the venturi formed at an end of a first portion of a protection tube, and flowing the exhaust from the venturi towards a sensor element through a plurality of perforations, the sensor element positioned within a second portion of the protection tube upstream of the venturi. In a first example of the method, the method may additionally or alternatively include increasing a rate of exhaust flow through the venturi relative to the rate of exhaust flow inside the exhaust passage, wherein the venturi is a variable area opening formed by coupling a region of increasing cross-section with a region of constant cross-section. A second example of the method optionally includes the first example, and further includes wherein the flowing includes flowing the exhaust from the venturi into the first portion of the protection tube in a direction opposite to a direction of exhaust flow inside the exhaust passage, directing the exhaust from the first portion into the second portion of the protection tube in a direction orthogonal to the direction of exhaust flow inside the exhaust passage, the second portion fluidically coupled to and orthogonal to the first portion, flowing the exhaust through the plurality of perforations towards the sensor element, and directing the exhaust out of the protection tube through an outlet. A third example of the method optionally includes one or more of the first and the second examples, and further includes wherein the plurality of perforations are formed on a baffle, the baffle coupled to a bottom plate, the bottom plate and the baffle positioned within the second portion, and wherein the sensor element is coupled to the bottom plate and faces towards the plurality of perforations. A fourth example of the method optionally includes one or more of the first through the third examples, and further includes wherein the protection tube is an inner tube positioned within an outer tube. A fifth example of the method optionally includes one or more of the first through the fourth examples, and further includes wherein the flowing further comprises includes flowing exhaust into a gap between the inner tube and the outer tube through an inlet formed on the outer tube, the inlet upstream of the venturi and the sensor element before flowing the exhaust into the venturi. A sixth example of the method optionally includes one or more of the first through the fifth examples, and further includes wherein the plurality of perforations are formed on a surface of the inner tube, the surface upstream of the venturi, and downstream of the sensor element, and wherein the sensor element is curved and positioned in the gap between the inner and the outer tube.

The systems and methods described above also provide for a particulate matter sensor comprising a particulate matter (PM) sensor assembly, comprising a protection tube having a vertical portion fluidically coupled to a horizontal portion, the vertical portion coupled to an exhaust pipe, and the horizontal portion having a venturi, a plurality of orifices formed within the vertical portion, and a sensor element positioned within the vertical portion, the sensor element upstream of the venturi, and a normal to the sensor element orthogonal to a surface having the plurality of orifices. In a first example of the particulate matter sensor assembly, the assembly may additionally or alternatively include wherein the venturi couples the horizontal portion to an opened up end, the opened up end having an outwardly increasing cross-section that directs exhaust into the horizontal portion and then towards the sensor element through the plurality of orifices and out of the assembly via a trapezoidal opening formed on the vertical portion, wherein the plurality of orifices are formed on a rectangular baffle positioned inside the vertical portion between a top end of the vertical portion and a bottom seal, the bottom located at a distance from the top end of the vertical portion, and wherein the sensor element includes interdigitated electrodes formed on a planar substrate located inside the vertical portion between the top end and the bottom seal. A second example of the particulate matter sensor optionally includes the first example and further includes wherein the protection tube is positioned within an outer tube and separated from the outer tube by a space, and wherein the outer tube includes a hole formed at a bent ("elbow") region of the outer tube, the hole configured to direct exhaust from the exhaust pipe first into the space, and then from the space towards the venturi formed on the inner tube towards the sensor element through the plurality of orifices, and subsequently out of the assembly through an open end of the outer tube, and wherein the plurality of orifices are formed on a region of the vertical portion upstream of the sensor element, and wherein the sensor element includes interdigitated electrodes formed on a curved substrate, the sensor element placed inside the space between the protection tube and the outer tube.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter (PM) sensor assembly, comprising:
   a bent tube located within an exhaust passage, the bent tube having a first closed end coupled to the exhaust passage and a second outwardly flared end including an outwardly angled portion within the exhaust passage;
   a plurality of perforations formed proximate to the first end; and
   a sensor element positioned facing towards the plurality of perforations, the sensor element located upstream of the second end.

2. The PM sensor assembly of claim 1, wherein the bent tube includes a first tube coupled to a second, orthogonal tube forming an L-shape, the first end of the bent tube formed at an end of the first tube, and the second end of the bent tube formed at an end of the second tube.

3. The PM sensor assembly of claim 2, wherein the first end is directly coupled to the exhaust passage, the first tube having a straight portion of uniform cross-section.

4. The PM sensor assembly of claim 3, wherein the second tube includes a straight portion of uniform cross-section coupled to the second end of the bent tube, and wherein the outwardly angled portion has increasing cross-section and is positioned inside the exhaust passage such that exhaust inside the exhaust passage reverses a direction of flow to enter the PM sensor assembly through the second end.

5. The PM sensor assembly of claim 2, wherein the first tube comprises:
   a bottom seal at a first distance from the first end of the bent tube, the bottom seal coupled to a first side surface of the first tube and at a first gap from a second, opposite side surface of the first tube, the bottom seal having a length that is smaller than a diameter of the first tube, the bottom seal separating the first tube into an upper chamber and a lower chamber;

a rectangular baffle having the plurality of perforations, a long axis of the baffle parallel to a long axis of the sensor element, wherein the sensor element is at a second gap from the baffle, the baffle and the sensor element positioned within the upper chamber of the first tube; and an outlet having a long axis parallel to the long axis of the sensor element.

6. The PM sensor assembly of claim 1, wherein the bent tube is an inner tube positioned within an outer, L-shaped, tube and separated from the outer tube by a space, the outer tube having a third, closed end coupled to the exhaust passage, and a fourth, open end positioned inside the exhaust passage, the fourth open end proximate to the second end of the inner tube.

7. The PM sensor assembly of claim 6, wherein the outer tube comprises an inlet upstream of the sensor element configured to direct exhaust from the exhaust passage into the space between the outer tube and the inner tube in a direction parallel to exhaust flow inside the exhaust passage.

8. The PM sensor assembly of claim 6, wherein the plurality of perforations are formed on a downstream side of the inner tube, and wherein the sensor element is positioned in the space between the inner tube and the outer tube facing towards the plurality of perforations.

9. The PM sensor assembly of claim 1, wherein the sensor element includes interdigitated electrodes formed on a curved substrate.

10. The PM sensor assembly of claim 1, further comprising:
a heating element coupled to the sensor element;
wherein the PM sensor assembly is coupled to a controller with computer readable instructions stored on non-transitory memory that when executed by a processor cause the controller to:
during exhaust flow, apply a first voltage to electrodes of the sensor element to accumulate exhaust particulate matter in the exhaust flow across the electrodes;
estimate a load on the PM sensor assembly based on a current generated across the electrodes of the sensor element; and
responsive to the load being higher than a threshold, apply a second, different voltage to the heating element to regenerate the sensor element.

11. A method, comprising:
reversing exhaust flow via a venturi formed at an end of a first horizontal portion of an L-shaped protection tube within an exhaust passage to direct exhaust from inside the exhaust passage towards the venturi; and
flowing the exhaust from the venturi towards a sensor element through a plurality of perforations, the sensor element positioned within a second vertical portion of the protection tube upstream of the venturi.

12. The method of claim 11, further comprising increasing a rate of exhaust flow through the venturi relative to a rate of exhaust flow inside the exhaust passage, wherein the venturi is a variable area opening formed by coupling a region of increasing cross-section with a region of constant cross-section.

13. The method of claim 11, wherein flowing the exhaust from the venturi towards the sensor element includes:
flowing the exhaust from the venturi into the first portion of the protection tube in a direction opposite to a direction of exhaust flow inside the exhaust passage;
directing the exhaust from the first portion into the second portion of the protection tube in a direction orthogonal to the direction of exhaust flow inside the exhaust passage, the second portion fluidically coupled to and orthogonal to the first portion;
flowing the exhaust through the plurality of perforations towards the sensor element; and
directing the exhaust out of the protection tube through an outlet.

14. The method of claim 11, wherein the plurality of perforations are formed on a baffle, the baffle coupled to a bottom plate, the bottom plate and the baffle positioned within the second portion, the bottom plate coupled to a first side surface of the second portion and at a first gap from a second, opposite side surface of the second portion, and wherein the sensor element is coupled to the bottom plate and faces towards the plurality of perforations; and further comprising increasing a rate of exhaust flow through the first gap.

15. The method of claim 11, wherein the protection tube is an inner tube positioned within an outer tube.

16. The method of claim 15, wherein flowing the exhaust from the venturi towards the sensor element further includes flowing exhaust into a gap between the inner tube and the outer tube through an inlet formed on the outer tube, the inlet upstream of each of the venturi and the sensor element before flowing the exhaust into the venturi.

17. The method of claim 16, wherein the plurality of perforations is formed on a surface of the inner tube, the surface upstream of the venturi and downstream of the sensor element, and wherein the sensor element is curved and positioned in the gap between the inner tube and the outer tube.

18. A particulate matter (PM) sensor assembly, comprising:
a protection tube having a vertical portion fluidically coupled to a horizontal portion, the vertical portion coupled to an exhaust pipe, and the horizontal portion having a venturi;
a plurality of orifices formed on a surface within the vertical portion; and
a sensor element positioned within the vertical portion, the sensor element upstream of the venturi, and a normal to the sensor element orthogonal to the surface having the plurality of orifices,
wherein the venturi couples the horizontal portion to an opened up end, the opened up end having an outwardly increasing cross-section that directs exhaust into the horizontal portion and then towards the sensor element through the plurality of orifices and out of the assembly via a trapezoidal opening formed on the vertical portion, wherein the plurality of orifices is formed on a rectangular baffle positioned inside the vertical portion between a top end of the vertical portion and a bottom seal, the bottom seal located at a distance from the top end of the vertical portion, and wherein the sensor element includes interdigitated electrodes formed on a planar substrate located inside the vertical portion between the top end and the bottom seal.

19. A particulate matter (PM) sensor assembly, comprising:
- a protection tube having a vertical portion fluidically coupled to a horizontal portion, the vertical portion coupled to an exhaust pipe, and the horizontal portion having a venturi;
- a plurality of orifices formed on a surface within the vertical portion; and
- a sensor element positioned within the vertical portion, the sensor element upstream of the venturi, and a normal to the sensor element orthogonal to the surface having the plurality of orifices,
- wherein the protection tube is positioned within an outer tube and separated from the outer tube by a space, and wherein the outer tube includes a hole formed at a bent region of the outer tube, the hole configured to direct exhaust from the exhaust pipe first into the space, and then from the space towards the venturi formed on the protection tube, then towards the sensor element through the plurality of orifices, and subsequently out of the PM sensor assembly through an open end of the outer tube, and wherein the plurality of orifices is formed on a region of the vertical portion upstream of the sensor element, and wherein the sensor element includes interdigitated electrodes formed on a curved substrate, the sensor element placed inside the space between the protection tube and the outer tube.

* * * * *